(12) United States Patent
Yamamoto et al.

(10) Patent No.: US 9,150,902 B2
(45) Date of Patent: Oct. 6, 2015

(54) METHOD FOR DETERMINATION OF N-DEACETYLASE/N-SULFOTRANSFERASE ACTIVITY

(75) Inventors: Koji Yamamoto, Higashiyamato (JP); Kiyoshi Suzuki, Higashiyamato (JP); Shuichi Miyaura, Higashiyamato (JP)

(73) Assignee: SEIKAGAKU CORPORATION, Tokyo (JP)

( * ) Notice: Subject to any disclaimer, the term of this patent is extended or adjusted under 35 U.S.C. 154(b) by 592 days.

(21) Appl. No.: 11/994,126

(22) PCT Filed: Jun. 28, 2006

(86) PCT No.: PCT/JP2006/312889
§ 371 (c)(1),
(2), (4) Date: Dec. 28, 2007

(87) PCT Pub. No.: WO2007/001021
PCT Pub. Date: Jan. 4, 2007

(65) Prior Publication Data
US 2009/0104627 A1    Apr. 23, 2009

(30) Foreign Application Priority Data
Jun. 28, 2005  (JP) ................................. 2005-188973

(51) Int. Cl.
*G01N 33/573* (2006.01)
*C12Q 1/48* (2006.01)
*C08B 37/00* (2006.01)
*G01N 33/543* (2006.01)

(52) U.S. Cl.
CPC .............. *C12Q 1/48* (2013.01); *C08B 37/0075* (2013.01); *C08B 37/0081* (2013.01); *G01N 33/543* (2013.01); *G01N 33/573* (2013.01); *G01N 2500/00* (2013.01)

(58) Field of Classification Search
CPC .................................................. G01N 33/573
See application file for complete search history.

(56) References Cited

U.S. PATENT DOCUMENTS

| | | | |
|---|---|---|---|
| 2003/0077763 A1 | 4/2003 | DeAngelis | |
| 2003/0109501 A1* | 6/2003 | Yang et al. | ..................... 514/102 |
| 2006/0116348 A1 | 6/2006 | DeAngelis | |
| 2009/0136964 A1 | 5/2009 | Suzuki et al. | |

FOREIGN PATENT DOCUMENTS

| | | |
|---|---|---|
| JP | 06145065 A | 5/1994 |
| JP | 2002-529064 A | 9/2002 |
| JP | 200418840 A | 1/2004 |
| JP | 4841546 B2 | 10/2011 |
| WO | 99/49018 A1 | 9/1999 |
| WO | 2004/068115 A2 | 8/2004 |

OTHER PUBLICATIONS

J. van den Born et al., "Antibody-Based Assay for N-deacetylase Activity of Heparan Sulfate/Heparin N-deacetylase/N-sulfotransferase (NDST): Novel Characteristics of NDST-1 and -2", Glycobiology 13(1): 1-10 (2003).*
G. David et al. "Developmental Changes in Heparan Sulfate Expression: In Situ Detection with mAbs", J. Cell Biology 119(4):961-975. (1992).*
J. Bengtsson et al. "Distinct Effects on Heparan Sulfate Structure by Different Active Site Mutations in NDST-1", Biochemistry 42:2110-2115. (2003).*
Renato V. Iozzo, "Presence of Unsulfated Heparan Chains on the Heparan Sulfate Proteoglycan of Human Colon Carcinoma Cells", The Journal of Biological Chemistry, Feb. 15, 1989, pp. 2690-2699, vol. 264, No. 5, The American Society for Biochemistry and Molecular Biology, Inc.
Dawn E. Verdugo et al., "A 96-well dot-blot assay for carbohydrate sulfotransferases", Analytical Biochemistry, 2002, pp. 330-336, vol. 307, Elsevier Science (USA).
Jacob Van Den Born et al., "Presence of N-Unsubstituted Glucosamine Units in Native Heparan Sulfate Revealed by a Monoclonal Antibody", The Journal of Biological Chemistry, Dec. 29, 1995, pp. 31303-31309, vol. 270, No. 52, The American Society for Biochemistry and Molecular Biology, Inc.
Extended European Search Report issued on Jun. 20, 2011, in corresponding European Patent Application No. 06767506.6 (in the name of Seikagaku Corporation).
Aikawa, J. et al., "Multiple Isozymes of Heparan Sulfate/Heparin GlcNAc N-Deacetylase/GlcN N-Sulfotransferase", The Journal of Biological Chemistry, Feb. 23, 2001, vol. 276, No. 8, pp. 5876-5882.
Brandan, E. et al., "Purification of Rat Liver N-Heparan-sulfate Sulfotransferase", The Journal of Biological Chemistry, Feb. 15, 1988, vol. 283, No. 5, pp. 2417-2422.
Communication from the Japanese Patent Office, dated Jan. 28, 2014, issued in counterpart Japanese Patent Application No. 2012-182378.
Tamura, J. et al., "Synthesis of Two Oligosaccharides," The Journal of Carbohydrate Chemistry, 1999, vol. 18, No. 1, pp. 2-15.
Japanese Office Action dated Jul. 3, 2012, issued by the Japanese Patent Office in counterpart Japanese Application No. 2007-523976.
Communication from the European Patent Office dated Feb. 8, 2012, issued in counterpart European Application No. 06767506.6 (in the name of Seikagaku Corporation).
Munoz, Eva et al., "Enzymatic synthesis of heparin related polysaccharides on sensor chips: Rapid screening of heparin-protein interactions", Biochemical and Biophysical Research Communications, Academic Press Inc., vol. 339, No. 2, Jan. 13, 2006, pp. 597-602.

* cited by examiner

*Primary Examiner* — Rebecca Prouty
(74) *Attorney, Agent, or Firm* — Sughrue Mion, PLLC

(57) ABSTRACT

A novel modified polysaccharide, a solid phase to which the polysaccharide is adhered, methods for detecting N-deacetylase activity, N-sulfotransferase activity and N-deacetylase/N-sulfotransferase activity in a sample which utilizes said solid phase, and detection kits thereof.

5 Claims, 8 Drawing Sheets

SEQUENCE LISTING

```
<160> NUMBER OF SEQ ID NOS: 8

<210> SEQ ID NO 1
<211> LENGTH: 2652
<212> TYPE: DNA
<213> ORGANISM: Homo sapiens
<220> FEATURE:
<221> NAME/KEY: CDS
<222> LOCATION: (1)..(2652)

<400> SEQUENCE: 1 atg ctc cag ttg tgg aag gtg gta cgc cca gct cgg cag ctg gaa ctg        48
Met Leu Gln Leu Trp Lys Val Val Arg Pro Ala Arg Gln Leu Glu Leu
1               5                   10                  15 cac cgc ctc ata ctg ctg ctg atc gct ttc agc ctg ggc tcc atg ggc        96
His Arg Leu Ile Leu Leu Leu Ile Ala Phe Ser Leu Gly Ser Met Gly
                20                  25                  30 ttc ctg gct tat tat gtg tcc acc agc cct aag gcc aag gaa ccc ttg       144
Phe Leu Ala Tyr Tyr Val Ser Thr Ser Pro Lys Ala Lys Glu Pro Leu
            35                  40                  45 ccc ctg ccc ttg gga gac tgc agc agc ggt ggg gca gct ggt cct ggc       192
Pro Leu Pro Leu Gly Asp Cys Ser Ser Gly Gly Ala Ala Gly Pro Gly
        50                  55                  60 cct gca cgg cct cca gtt cca cct cgg ccc ccc agg cct cca gag aca       240
Pro Ala Arg Pro Pro Val Pro Pro Arg Pro Pro Arg Pro Pro Glu Thr
65                  70                  75                  80 gct cga act gaa ccc gtg gtc ctt gtg ttt gtg gag agt gca tac tca       288
Ala Arg Thr Glu Pro Val Val Leu Val Phe Val Glu Ser Ala Tyr Ser
                85                  90                  95 cag ctg ggg cag gaa att gtg gcc atc ctg gag tct agt cgt ttt cgt       336
Gln Leu Gly Gln Glu Ile Val Ala Ile Leu Glu Ser Ser Arg Phe Arg
                100                 105                 110 tat agc act gag ttg gca cct ggc cga ggg gac atg ccc aca ttg act       384
Tyr Ser Thr Glu Leu Ala Pro Gly Arg Gly Asp Met Pro Thr Leu Thr
            115                 120                 125 gat aat acc cat ggc cgc tat gtc ttg gtc att tat gag aac ctg ctc       432
Asp Asn Thr His Gly Arg Tyr Val Leu Val Ile Tyr Glu Asn Leu Leu
        130                 135                 140 aag tat gtc aac ctg gat gcc tgg agt cgg gaa ctg cta gac cgg tac       480
Lys Tyr Val Asn Leu Asp Ala Trp Ser Arg Glu Leu Leu Asp Arg Tyr
145                 150                 155                 160 tgc gtg gag tat ggt gtg ggc atc att ggc ttt tcg gcc cac gag       528
Cys Val Glu Tyr Gly Val Gly Ile Ile Gly Phe Phe Arg Ala His Glu
                165                 170                 175 cac agc cta ctg agc gcc cag ctc aag ggc ttt ccc ctt ttt tta cac       576
His Ser Leu Leu Ser Ala Gln Leu Lys Gly Phe Pro Leu Phe Leu His
                180                 185                 190 tca aac ttg ggg ctc cgg gac tac caa gtg aat cct tct gcc ccg cta       624
Ser Asn Leu Gly Leu Arg Asp Tyr Gln Val Asn Pro Ser Ala Pro Leu
            195                 200                 205 ctg cat ctc aca cgc ccc agc cgc cta gaa cca ggg cca ctg cct ggt       672
```

| | | | | | | | | | | | | |
|---|---|---|---|---|---|---|---|---|---|---|---|---|
| Leu | His | Leu | Thr | Arg | Pro | Ser | Arg | Leu | Glu | Pro | Gly | Pro | Leu | Pro | Gly |
| | 210 | | | | 215 | | | | 220 | | | | | | |

| gat | gac | tgg | acc | atc | ttc | caa | tcc | aat | cat | agt | aca | tat | gaa | cca | gtg | 720 |
|---|---|---|---|---|---|---|---|---|---|---|---|---|---|---|---|---|
| Asp | Asp | Trp | Thr | Ile | Phe | Gln | Ser | Asn | His | Ser | Thr | Tyr | Glu | Pro | Val | |
| 225 | | | | | 230 | | | | | 235 | | | | | 240 | |

| ctt | ctt | gcc | agc | ctt | cgg | cca | gct | gag | ccc | gca | gtg | cca | gga | cca | gtt | 768 |
|---|---|---|---|---|---|---|---|---|---|---|---|---|---|---|---|---|
| Leu | Leu | Ala | Ser | Leu | Arg | Pro | Ala | Glu | Pro | Ala | Val | Pro | Gly | Pro | Val | |
| | | | | 245 | | | | | 250 | | | | | 255 | | |

| ctt | cgt | cgg | gcc | cgg | ctt | ccc | act | gtg | gta | cag | gac | ctg | ggg | ctt | cat | 816 |
|---|---|---|---|---|---|---|---|---|---|---|---|---|---|---|---|---|
| Leu | Arg | Arg | Ala | Arg | Leu | Pro | Thr | Val | Val | Gln | Asp | Leu | Gly | Leu | His | |
| | | | 260 | | | | | 265 | | | | | 270 | | | |

| gat | ggc | atc | cag | cgg | gtg | ctc | ttt | gga | cat | ggc | ctt | tcc | ttc | tgg | ctc | 864 |
|---|---|---|---|---|---|---|---|---|---|---|---|---|---|---|---|---|
| Asp | Gly | Ile | Gln | Arg | Val | Leu | Phe | Gly | His | Gly | Leu | Ser | Phe | Trp | Leu | |
| | | | 275 | | | | | 280 | | | | | 285 | | | |

| cac | aaa | ctt | atc | ttc | gtt | gat | gct | gtt | gca | tac | ctc | act | ggc | aag | cgc | 912 |
|---|---|---|---|---|---|---|---|---|---|---|---|---|---|---|---|---|
| His | Lys | Leu | Ile | Phe | Val | Asp | Ala | Val | Ala | Tyr | Leu | Thr | Gly | Lys | Arg | |
| | 290 | | | | | 295 | | | | | 300 | | | | | |

| ctc | tgc | ctg | gac | ctt | gac | cgc | tac | atc | ttg | gta | gac | atc | gat | gac | atc | 960 |
|---|---|---|---|---|---|---|---|---|---|---|---|---|---|---|---|---|
| Leu | Cys | Leu | Asp | Leu | Asp | Arg | Tyr | Ile | Leu | Val | Asp | Ile | Asp | Asp | Ile | |
| 305 | | | | | 310 | | | | | 315 | | | | | 320 | |

| ttt | gtg | ggc | aag | gaa | ggg | acc | cgc | atg | aag | gtg | gct | gat | gtt | gag | gct | 1008 |
|---|---|---|---|---|---|---|---|---|---|---|---|---|---|---|---|---|
| Phe | Val | Gly | Lys | Glu | Gly | Thr | Arg | Met | Lys | Val | Ala | Asp | Val | Glu | Ala | |
| | | | | 325 | | | | | 330 | | | | | 335 | | |

| ctg | ttg | acc | acc | cag | aac | aaa | ctc | agg | acc | tta | gtt | ccc | aac | ttc | acc | 1056 |
|---|---|---|---|---|---|---|---|---|---|---|---|---|---|---|---|---|
| Leu | Leu | Thr | Thr | Gln | Asn | Lys | Leu | Arg | Thr | Leu | Val | Pro | Asn | Phe | Thr | |
| | | | 340 | | | | | 345 | | | | | 350 | | | |

| ttc | aac | ttg | ggc | ttc | tcg | ggc | aag | ttc | tat | cat | act | ggg | aca | gag | gag | 1104 |
|---|---|---|---|---|---|---|---|---|---|---|---|---|---|---|---|---|
| Phe | Asn | Leu | Gly | Phe | Ser | Gly | Lys | Phe | Tyr | His | Thr | Gly | Thr | Glu | Glu | |
| | | 355 | | | | | 360 | | | | | 365 | | | | |

| gag | gat | gca | ggg | gac | gac | atg | ctg | ctg | aag | cac | cgc | aaa | gag | ttc | tgg | 1152 |
|---|---|---|---|---|---|---|---|---|---|---|---|---|---|---|---|---|
| Glu | Asp | Ala | Gly | Asp | Asp | Met | Leu | Leu | Lys | His | Arg | Lys | Glu | Phe | Trp | |
| 370 | | | | | 375 | | | | | 380 | | | | | | |

| tgg | ttc | ccc | cac | atg | tgg | agc | cac | atg | cag | cca | cac | ctg | ttc | cac | aat | 1200 |
|---|---|---|---|---|---|---|---|---|---|---|---|---|---|---|---|---|
| Trp | Phe | Pro | His | Met | Trp | Ser | His | Met | Gln | Pro | His | Leu | Phe | His | Asn | |
| 385 | | | | 390 | | | | | 395 | | | | | 400 | | |

| cgc | tcc | gtg | ctg | gct | gac | cag | atg | agg | ctc | aac | aaa | cag | ttt | gct | ctg | 1248 |
|---|---|---|---|---|---|---|---|---|---|---|---|---|---|---|---|---|
| Arg | Ser | Val | Leu | Ala | Asp | Gln | Met | Arg | Leu | Asn | Lys | Gln | Phe | Ala | Leu | |
| | | | | 405 | | | | | 410 | | | | | 415 | | |

| gag | cat | ggg | att | ccc | acg | gac | ctg | ggg | tat | gct | gtg | gcc | ccc | cac | cac | 1296 |
|---|---|---|---|---|---|---|---|---|---|---|---|---|---|---|---|---|
| Glu | His | Gly | Ile | Pro | Thr | Asp | Leu | Gly | Tyr | Ala | Val | Ala | Pro | His | His | |
| | | | 420 | | | | | 425 | | | | | 430 | | | |

| tcg | ggt | gtg | tac | ccc | atc | cac | acg | cag | ctc | tat | gag | gcc | tgg | aaa | tcc | 1344 |
|---|---|---|---|---|---|---|---|---|---|---|---|---|---|---|---|---|
| Ser | Gly | Val | Tyr | Pro | Ile | His | Thr | Gln | Leu | Tyr | Glu | Ala | Trp | Lys | Ser | |
| | | | 435 | | | | | 440 | | | | | 445 | | | |

| gtg | tgg | ggc | atc | cag | gtg | acc | agc | act | gag | gag | tat | ccc | cat | ctc | cgc | 1392 |
|---|---|---|---|---|---|---|---|---|---|---|---|---|---|---|---|---|
| Val | Trp | Gly | Ile | Gln | Val | Thr | Ser | Thr | Glu | Glu | Tyr | Pro | His | Leu | Arg | |
| 450 | | | | | 455 | | | | | 460 | | | | | | |

| cct | gcc | cgc | tac | cgc | cgt | ggc | ttc | att | cac | aat | ggc | att | atg | gtg | ctg | 1440 |
|---|---|---|---|---|---|---|---|---|---|---|---|---|---|---|---|---|
| Pro | Ala | Arg | Tyr | Arg | Arg | Gly | Phe | Ile | His | Asn | Gly | Ile | Met | Val | Leu | |
| 465 | | | | 470 | | | | | 475 | | | | | 480 | | |

| ccc | cgg | cag | aca | tgt | ggc | ctc | ttc | act | cac | aca | atc | ttc | tat | aat | gag | 1488 |
|---|---|---|---|---|---|---|---|---|---|---|---|---|---|---|---|---|
| Pro | Arg | Gln | Thr | Cys | Gly | Leu | Phe | Thr | His | Thr | Ile | Phe | Tyr | Asn | Glu | |
| | | | | 485 | | | | | 490 | | | | | 495 | | |

| tat | cct | gga | ggc | tct | cgt | gaa | cta | gac | cgg | agc | atc | cga | ggt | gga | gag | 1536 |
|---|---|---|---|---|---|---|---|---|---|---|---|---|---|---|---|---|
| Tyr | Pro | Gly | Gly | Ser | Arg | Glu | Leu | Asp | Arg | Ser | Ile | Arg | Gly | Gly | Glu | |
| | | | 500 | | | | | 505 | | | | | 510 | | | |

| ctc | ttt | ctg | aca | gtg | ctg | ctt | aat | ccg | atc | agc | atc | ttt | atg | acc | cat | 1584 |
|---|---|---|---|---|---|---|---|---|---|---|---|---|---|---|---|---|
| Leu | Phe | Leu | Thr | Val | Leu | Leu | Asn | Pro | Ile | Ser | Ile | Phe | Met | Thr | His | |
| | | 515 | | | | | 520 | | | | | 525 | | | | |

```
                                                        -continued ctg tcc aat tat gga aat gac cgg ctg ggc cta tac acc ttt gag agc    1632
Leu Ser Asn Tyr Gly Asn Asp Arg Leu Gly Leu Tyr Thr Phe Glu Ser
    530             535                 540 ttg gtg cgc ttc ctc cag tgt tgg aca cgg ctg cgc cta cag acc ctt    1680
Leu Val Arg Phe Leu Gln Cys Trp Thr Arg Leu Arg Leu Gln Thr Leu
545                 550                 555                 560 cct cct gtc cca ctt gca cag aag tac ttt gaa ctt ttc cct cag gag    1728
Pro Pro Val Pro Leu Ala Gln Lys Tyr Phe Glu Leu Phe Pro Gln Glu
                565                 570                 575 cga agc ccc ctt tgg cag aat ccc tgt gat gac aag agg cac aaa gat    1776
Arg Ser Pro Leu Trp Gln Asn Pro Cys Asp Asp Lys Arg His Lys Asp
            580                 585                 590 atc tgg tcc aag gag aaa acc tgt gat cgt ctc ccg aag ttc ctc att    1824
Ile Trp Ser Lys Glu Lys Thr Cys Asp Arg Leu Pro Lys Phe Leu Ile
        595                 600                 605 gtg gga ccc cag aaa aca ggg act aca gct att cac ttc ttc ctg agc    1872
Val Gly Pro Gln Lys Thr Gly Thr Thr Ala Ile His Phe Phe Leu Ser
    610             615                 620 ctg cac cca gct gta act agc agc ttc cct agc ccc agc aca ttt gag    1920
Leu His Pro Ala Val Thr Ser Ser Phe Pro Ser Pro Ser Thr Phe Glu
625                 630                 635                 640 gag att cag ttc ttc aac agc cct aat tac cac aag ggt att gac tgg    1968
Glu Ile Gln Phe Phe Asn Ser Pro Asn Tyr His Lys Gly Ile Asp Trp
                645                 650                 655 tac atg gat ttc ttc cct gtt cct tcc aat gcc agc act gat ttc cta    2016
Tyr Met Asp Phe Phe Pro Val Pro Ser Asn Ala Ser Thr Asp Phe Leu
            660                 665                 670 ttt gaa aaa agt gcc acc tac ttt gac tct gaa gtt gta cca cgg cgg    2064
Phe Glu Lys Ser Ala Thr Tyr Phe Asp Ser Glu Val Val Pro Arg Arg
        675                 680                 685 ggg gct gcc ctc ctg cca cga gcc aag atc atc aca gtg ctc acc aac    2112
Gly Ala Ala Leu Leu Pro Arg Ala Lys Ile Ile Thr Val Leu Thr Asn
    690             695                 700 cct gct gac agg gcc tac tcc tgg tac cag cat cag cga gcc cat gga    2160
Pro Ala Asp Arg Ala Tyr Ser Trp Tyr Gln His Gln Arg Ala His Gly
705                 710                 715                 720 gac cca gtt gct ctg aac tat acc ttc tat cag gtg att tca gcc tcc    2208
Asp Pro Val Ala Leu Asn Tyr Thr Phe Tyr Gln Val Ile Ser Ala Ser
                725                 730                 735 tcc cag acc cct ctg gca cta cgc tcc ctg cag aac cgc tgt ctt gtc    2256
Ser Gln Thr Pro Leu Ala Leu Arg Ser Leu Gln Asn Arg Cys Leu Val
            740                 745                 750 cct ggc tac tat tct acc cat cta caa cgc tgg ctg act tac tac ccc    2304
Pro Gly Tyr Tyr Ser Thr His Leu Gln Arg Trp Leu Thr Tyr Tyr Pro
        755                 760                 765 tct gga cag ttg ctg att gtg gat ggg caa gag ctg cgt acc aac cca    2352
Ser Gly Gln Leu Leu Ile Val Asp Gly Gln Glu Leu Arg Thr Asn Pro
    770             775                 780 gca gcc tca atg gag agc atc cag aag ttc ctg ggt atc aca ccc ttt    2400
Ala Ala Ser Met Glu Ser Ile Gln Lys Phe Leu Gly Ile Thr Pro Phe
785                 790                 795                 800 ctg aac tac aca cgg acc ctc agg ttt gat gat gat aag gga ttt tgg    2448
Leu Asn Tyr Thr Arg Thr Leu Arg Phe Asp Asp Asp Lys Gly Phe Trp
                805                 810                 815 tgc cag gga ctt gaa ggt ggt aag act cgc tgt cta gcc ggg agc aaa    2496
Cys Gln Gly Leu Glu Gly Gly Lys Thr Arg Cys Leu Ala Gly Ser Lys
            820                 825                 830 ggc cgg agg tat cca gat atg gac act gag tcc cgt ctt ttc ctt acg    2544
Gly Arg Arg Tyr Pro Asp Met Asp Thr Glu Ser Arg Leu Phe Leu Thr
        835                 840                 845
```

-continued

```
gat ttt ttc cgg aac cat aat ttg gag ttg tcg aag ctg ctg agc cgg    2592
Asp Phe Phe Arg Asn His Asn Leu Glu Leu Ser Lys Leu Leu Ser Arg
850                 855                 860 ctt gga cag cca gtg ccc tcg tgg ctt cgg gaa gaa ctg cag cat tcc    2640
Leu Gly Gln Pro Val Pro Ser Trp Leu Arg Glu Glu Leu Gln His Ser
865                 870                 875                 880 agt ctg ggc tga                                                     2652
Ser Leu Gly
```

<210> SEQ ID NO 2
<211> LENGTH: 883
<212> TYPE: PRT
<213> ORGANISM: Homo sapiens

<400> SEQUENCE: 2

```
Met Leu Gln Leu Trp Lys Val Val Arg Pro Ala Arg Gln Leu Glu Leu
1               5                   10                  15

His Arg Leu Ile Leu Leu Ile Ala Phe Ser Leu Gly Ser Met Gly
            20                  25                  30

Phe Leu Ala Tyr Tyr Val Ser Thr Ser Pro Lys Ala Lys Glu Pro Leu
        35                  40                  45

Pro Leu Pro Leu Gly Asp Cys Ser Ser Gly Gly Ala Gly Pro Gly
    50                  55                  60

Pro Ala Arg Pro Pro Val Pro Arg Pro Pro Arg Pro Pro Glu Thr
65                  70                  75                  80

Ala Arg Thr Glu Pro Val Val Leu Val Phe Val Glu Ser Ala Tyr Ser
                85                  90                  95

Gln Leu Gly Gln Glu Ile Val Ala Ile Leu Glu Ser Ser Arg Phe Arg
            100                 105                 110

Tyr Ser Thr Glu Leu Ala Pro Gly Arg Gly Asp Met Pro Thr Leu Thr
        115                 120                 125

Asp Asn Thr His Gly Arg Tyr Val Leu Val Ile Tyr Glu Asn Leu Leu
    130                 135                 140

Lys Tyr Val Asn Leu Asp Ala Trp Ser Arg Glu Leu Leu Asp Arg Tyr
145                 150                 155                 160

Cys Val Glu Tyr Gly Val Gly Ile Ile Gly Phe Arg Ala His Glu
                165                 170                 175

His Ser Leu Leu Ser Ala Gln Leu Lys Gly Phe Pro Leu Phe Leu His
            180                 185                 190

Ser Asn Leu Gly Leu Arg Asp Tyr Gln Val Asn Pro Ser Ala Pro Leu
        195                 200                 205

Leu His Leu Thr Arg Pro Ser Arg Leu Glu Pro Gly Pro Leu Pro Gly
    210                 215                 220

Asp Asp Trp Thr Ile Phe Gln Ser Asn His Ser Thr Tyr Glu Pro Val
225                 230                 235                 240

Leu Leu Ala Ser Leu Arg Pro Ala Glu Pro Ala Val Pro Gly Pro Val
                245                 250                 255

Leu Arg Arg Ala Arg Leu Pro Thr Val Val Gln Asp Leu Gly Leu His
            260                 265                 270

Asp Gly Ile Gln Arg Val Leu Phe Gly His Gly Leu Ser Phe Trp Leu
        275                 280                 285

His Lys Leu Ile Phe Val Asp Ala Val Ala Tyr Leu Thr Gly Lys Arg
    290                 295                 300

Leu Cys Leu Asp Leu Asp Arg Tyr Ile Leu Val Asp Ile Asp Asp Ile
305                 310                 315                 320
```

-continued

Phe Val Gly Lys Glu Gly Thr Arg Met Lys Val Ala Asp Val Glu Ala
                325                 330                 335

Leu Leu Thr Thr Gln Asn Lys Leu Arg Thr Leu Val Pro Asn Phe Thr
            340                 345                 350

Phe Asn Leu Gly Phe Ser Gly Lys Phe Tyr His Thr Gly Thr Glu Glu
        355                 360                 365

Glu Asp Ala Gly Asp Met Leu Leu Lys His Arg Lys Glu Phe Trp
    370                 375                 380

Trp Phe Pro His Met Trp Ser His Met Gln Pro His Leu Phe His Asn
385                 390                 395                 400

Arg Ser Val Leu Ala Asp Gln Met Arg Leu Asn Lys Gln Phe Ala Leu
                405                 410                 415

Glu His Gly Ile Pro Thr Asp Leu Gly Tyr Ala Val Ala Pro His His
            420                 425                 430

Ser Gly Val Tyr Pro Ile His Thr Gln Leu Tyr Glu Ala Trp Lys Ser
        435                 440                 445

Val Trp Gly Ile Gln Val Thr Ser Thr Glu Glu Tyr Pro His Leu Arg
    450                 455                 460

Pro Ala Arg Tyr Arg Arg Gly Phe Ile His Asn Gly Ile Met Val Leu
465                 470                 475                 480

Pro Arg Gln Thr Cys Gly Leu Phe Thr His Thr Ile Phe Tyr Asn Glu
                485                 490                 495

Tyr Pro Gly Gly Ser Arg Glu Leu Asp Arg Ser Ile Arg Gly Gly Glu
            500                 505                 510

Leu Phe Leu Thr Val Leu Leu Asn Pro Ile Ser Ile Phe Met Thr His
        515                 520                 525

Leu Ser Asn Tyr Gly Asn Asp Arg Leu Gly Leu Tyr Thr Phe Glu Ser
    530                 535                 540

Leu Val Arg Phe Leu Gln Cys Trp Thr Arg Leu Arg Leu Gln Thr Leu
545                 550                 555                 560

Pro Pro Val Pro Leu Ala Gln Lys Tyr Phe Glu Leu Phe Pro Gln Glu
                565                 570                 575

Arg Ser Pro Leu Trp Gln Asn Pro Cys Asp Asp Lys Arg His Lys Asp
            580                 585                 590

Ile Trp Ser Lys Glu Lys Thr Cys Asp Arg Leu Pro Lys Phe Leu Ile
        595                 600                 605

Val Gly Pro Gln Lys Thr Gly Thr Thr Ala Ile His Phe Phe Leu Ser
    610                 615                 620

Leu His Pro Ala Val Thr Ser Ser Phe Pro Ser Pro Ser Thr Phe Glu
625                 630                 635                 640

Glu Ile Gln Phe Phe Asn Ser Pro Asn Tyr His Lys Gly Ile Asp Trp
                645                 650                 655

Tyr Met Asp Phe Phe Pro Val Pro Ser Asn Ala Ser Thr Asp Phe Leu
            660                 665                 670

Phe Glu Lys Ser Ala Thr Tyr Phe Asp Ser Glu Val Pro Arg Arg
    675                 680                 685

Gly Ala Ala Leu Leu Pro Arg Ala Lys Ile Ile Thr Val Leu Thr Asn
    690                 695                 700

Pro Ala Asp Arg Ala Tyr Ser Trp Tyr Gln His Gln Arg Ala His Gly
705                 710                 715                 720

Asp Pro Val Ala Leu Asn Tyr Thr Phe Tyr Gln Val Ile Ser Ala Ser
                725                 730                 735

```
Ser Gln Thr Pro Leu Ala Leu Arg Ser Leu Gln Asn Arg Cys Leu Val
            740                 745                 750

Pro Gly Tyr Tyr Ser Thr His Leu Gln Arg Trp Leu Thr Tyr Tyr Pro
        755                 760                 765

Ser Gly Gln Leu Leu Ile Val Asp Gly Gln Glu Leu Arg Thr Asn Pro
        770                 775                 780

Ala Ala Ser Met Glu Ser Ile Gln Lys Phe Leu Gly Ile Thr Pro Phe
785                 790                 795                 800

Leu Asn Tyr Thr Arg Thr Leu Arg Phe Asp Asp Lys Gly Phe Trp
                805                 810                 815

Cys Gln Gly Leu Glu Gly Gly Lys Thr Arg Cys Leu Gly Arg Ser Lys
            820                 825                 830

Gly Arg Arg Tyr Pro Asp Met Asp Thr Glu Ser Arg Leu Phe Leu Thr
            835                 840                 845

Asp Phe Phe Arg Asn His Asn Leu Glu Leu Ser Lys Leu Leu Ser Arg
850                 855                 860

Leu Gly Gln Pro Val Pro Ser Trp Leu Arg Glu Glu Leu Gln His Ser
865                 870                 875                 880

Ser Leu Gly

<210> SEQ ID NO 3
<211> LENGTH: 49
<212> TYPE: DNA
<213> ORGANISM: Artificial Sequence
<220> FEATURE:
<223> OTHER INFORMATION: Synthetic oligonucleotide primer

<400> SEQUENCE: 3
gatcggatcc aactcctaaa aaaccgccac catgctgcta gtaaatcag         49

<210> SEQ ID NO 4
<211> LENGTH: 45
<212> TYPE: DNA
<213> ORGANISM: Artificial Sequence
<220> FEATURE:
<223> OTHER INFORMATION: Synthetic oligonucleotide primer

<400> SEQUENCE: 4
cacgggttca gttcgagctg tctccgcaaa ggcagaatgc gccgc             45

<210> SEQ ID NO 5
<211> LENGTH: 21
<212> TYPE: DNA
<213> ORGANISM: Artificial Sequence
<220> FEATURE:
<223> OTHER INFORMATION: Synthetic lobster L21 sequence

<400> SEQUENCE: 5
aactcctaaa aaaccgccac c                                       21

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 6
gagacagctc gaactgaacc cgtgg                                   25

<210> SEQ ID NO 7
```

```
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 7
ctggtatggc ggccgcaatt gtcagcccag actggaatgc tgcagttc                 48

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 8
gatcggatcc aactcctaaa aaaccgccac                                     30
```

METHOD FOR DETERMINATION OF N-DEACETYLASE/N-SULFOTRANSFERASE ACTIVITY

TECHNICAL FIELD

The present invention relates to a novel modified polysaccharide, a solid phase to which said polysaccharide is adhered, methods for detecting N-deacetylase activity, N-sulfotransferase activity and N-deacetylase/N-sulfotransferase activity in a sample and detection kits thereof.

BACKGROUND OF THE INVENTION

The abbreviations to be used in the application documents are as follows.
BSA: bovine serum albumin
EDC: 1-ethyl-3-(3-dimethylaminopropyl)carbodiimide
EDNA: ethylenediamine tetraacetic acid
ELISA: enzyme-linked immunosorbent assay
GlcA: glucuronic acid
GlcN: glucosamine
GlcNAc: N-acetylglucosamine
HEPES: 2-[4-(2-hydroxyethyl)-1-piperazinyl]ethanesulfonic acid
HP: heparin
HPLC: high-performance liquid chromatography
HRP: horseradish peroxidase
HS: heparan sulfate
IgG: immunoglobulin G
MES: 2-morpholinoethanesulfonic acid
NAH: N-acetyl heparosan
ND: N-deacetylase
NDST: N-deacetylase/N-sulfotransferase
PAPS: 5'-phosphoadenosine 3'-phosphosulfate
PBS: phosphate buffered saline
PCR: polymerase chain reaction
PDP: 2-pyridyldisulfidepropionyl
RIA: radioimmunoassay
SDS: sodium dodecyl sulfate
SPDP: N-succinimidyl-3-(2-pyridylthio)propionate
SS bond: disulfide bond
ST: N-sulfotransferase
TBS: Tris-HCl buffered saline
TMB: 3,3',5,5'-tetramethylbenzidine NDST is an enzyme which is concerned in the synthesis of HP and HS, and is an enzyme that has both of the ND activity and ST activity. It has been reported that 4 species of variants (NDST 1, NDST 2, NDST 3 and NDST 4) are present in NDST and their substrate specificity and the like are different from one another. For example, ND activity of NDST 3 is high and ST activity thereof is low. On the other hand, ND activity of NDST 4 is low and ST activity thereof is markedly high (Non-patent Reference 1).

It has been reported that NDST 1 knockout mice are newborn-lethal. On the other hand, although NDST 2 knockout mice do not show lethality, reduction of granules inside the mast cell, reduction of HP negative charge, reduction of the histamine content to $\frac{1}{170}$ and the like changes have been reported (Non-patent References 2 to 8). Thus, there is a possibility that NDST is concerned in the diseases caused by such phenomena in the living body.

Regarding the method for measuring NDST activity, a measuring method which uses a substrate labeled with a radioisotope is known. According to the method, using NAH in which the acetyl group of GlcNAc residue is labeled with a radioisotope ($^3$H) as a substrate, the ND activity of NDST is measured by measuring the amount of $CH_3COO^3H$ released from the substrate by the enzymatic activity. Additionally, the ST activity of NDST is measured using PAPS labeled with a radioisotope ($^{35}$S) and N-desulfated HP or N-desulfated HS, by measuring the incorporated amount of N-sulfate ($^{35}$S) of said polysaccharide by the enzymatic activity (Non-patent References 1, 12 to 15, Patent Reference 1).

Additionally, although the methods for measuring NDST activity which do not use radioisotope are also known, only a sandwich ELISA method which uses a monoclonal antibody JM403 (Non-patent References 9 and 10) and an HPLC method which uses heparinase digests of the reaction product have been reported.

Although the former measuring method is a method which uses the reaction of de-N-acetylated region formed by ND with the antibody JM403, it requires two or more epitopes since it is a sandwich method. Additionally, the ST activity cannot be detected by the method (Non-patent Reference 11).

Although the latter measuring method is a method in which de-N-acetylation degree and N-sulfation degree of the de-N-acetylated NAH formed by the ND activity and ST activity and the unsaturated disaccharide obtained by the heparinase digestion of N-sulfated NAH are calculated using the "2-8 structural analysis as a combination of glycosaminoglycan degrading enzyme and HPLC" described in Non-patent Reference 16, it is not suited for chromatography, screening and the like methods for measuring activity of multiple samples (Patent Reference 2, Non-patent Reference 17).

When activities of ND, ST and NDST can be measured conveniently and quickly with high sensitivity and high accuracy and also at a moderate price, not only the detection, morbid state understanding and the like of diseases in which such enzymes are concerned and risks thereof can be easily carried out, but also screening and the like of substances which provide changes in the activities of said enzymes (inhibitors, activators and the like) can be carried out efficiently.
Patent Reference 1: US 2003/0109501A
Patent Reference 2: US 2004/0043447A
Non-patent Reference 1: Aikawa, J. et al., 2001, *Journal of Biological Chemistry*, vol. 276, no. 8, p. 5876-5882
Non-patent Reference Z: Humphries, D. E. et al., 1999, Nature, vol. 400, p. 769-772
Non-patent Reference 3: Forsberg, E. et al., 1999, Nature, vol. 400, p. 773-776
Non-patent Reference 4: Ringivall, M. et al., 2000, *Journal of Biological Chemistry*, vol. 275, no. 34, p. 25926-25930
Non-patent Reference 5: Pikas, D. E. et al., 2000, *Biochemistry*, vol. 39, p. 4552-4558
Non-patent Reference 6: Fukuda, M. et al., 2001, *Journal of Biological Chemistry*, vol. 276, no. 51, p. 47747-47750
Non-patent Reference 7: Esko, J. D. et al., 2001, *Journal of Clinical Investigation*, vol. 108, p. 169-173
Non-patent Reference S: Forsberg, E. et al., 2001, *Journal of Clinical Investigation*, vol, 108, p. 175-180
Non-patent Reference 9: van den Born, J. et al., 1992, *Kidney International*, vol. 41, p. 115-123
Non-patent Reference 10: van den Born, Y. et al., 1995, *Journal of Biological Chemistry*, vol. 270, no. 52, p. 31303-31309
Non-patent Reference 11: van den Born, J. et al., 2003, *Glycobiology*, vol. 13, no. 1, p. 1-10
Non-patent Reference 12: Brandan, E. et al, 1988, *Journal of Biological Chemistry*, vol. 263, no. 5, p. 2417-2422
Non-patent Reference 13: Bame, K. J. et al., 1991, *Journal of Biological Chemistry*, vol. 266, no. 16, p. 10287-10293
Non-patent Reference 14: Bame, K. J. et al., 1991, *Journal of Biological Chemistry*, vol. 266, no. 19, p. 12461-12468

Non-patent Reference 15: Verdugo, D. E. et al., 2002, *Analytical Biochemistry*, vol. 307, p. 330-336

Non-patent Reference 16: Shin Seikagaku Jikken Koza 3, Toshitsu II (published by Tokyo Kagaku Dojin, 1991), p. 49-62

Non-patent Reference 17: Saribas, A. S. et al., 2004, *Glycobiology*, vol. 14, no. 12, p. 1217-1228

DISCLOSURE OF THE INVENTION

Problems to be Solved by the Invention

The present invention aims at providing methods and kits which can measure activities of a group of enzymes which are concerned in the biosynthesis of HP/HS, particularly NI, ST and NDST, conveniently and quickly with high sensitivity and high accuracy and also at a moderate price, and a screening method and the like of substances which change activities of these enzymes.

Means for Solving the Problems

The inventors of the present invention have conducted intensive studies with the aim of solving the aforementioned problems and found that activities of ND, ST and NDST can be measured conveniently and quickly with high sensitivity and high accuracy and also at a moderate price by producing and using a modified polysaccharide in which a specific substance binds to NAH or a derivative thereof. Based on this, it became able to provide methods and kits which can measure activities of ND, ST and NDST conveniently and quickly with high sensitivity and high accuracy and also at a moderate price and screening methods of substances which change activities of these enzymes. As a result, the present invention is accomplished.

Namely, the present invention provides a modified polysaccharide, in which a substance selected from the following group binds to NAH or derivative thereof (to be referred to as "polysaccharide of the present invention" hereinafter).

(Group) Protein, Biotin, Antigenic Substance

It is preferable that this bond is formed between the aforementioned substance and the reducing end of NAH or a derivative thereof. It is also preferable that binding with a protein among them is a covalent bond or an affinity bond. The covalent bond is preferably SS bond or amido bond, and this affinity bond is preferably biotin-avidin bond. Also, it is preferable that this protein is a soluble protein having a molecular weight of from 15,000 to 200,000. It is preferable that the "soluble protein having a molecular weight of from 15,000 to 200,000" is immunoglobulin, avidin, protein A, protein G, albumin or casein. It is preferable that the albumin is serum albumin or egg albumin. Additionally, it is preferable that the derivative of NAH is a substance selected from the group consisting of the following (1) to (3):
(1) N-desulfated HP or N-desulfated/N-acetylated HP
(2) N-desulfated HS or N-desulfated/N-acetylated HS
(3) de-N-acetylated NAH.

The present invention also provides a solid phase to which the polysaccharide of the present invention is adhered (to be referred to as "solid phase of the present invention" hereinafter).

The present invention also provides a method for detecting ND activity in a sample, which comprises at least the following steps (a) and (b) (to be referred to as "ND detection method of the present invention" hereinafter):

step (a): a step for allowing a sample to contact with the solid phase of the present invention and step (b): a step for detecting de-N-acetylation in the polysaccharide of the present invention adhered to the aforementioned solid phase.

It is preferable that the detection of de-N-acetylation is carried out by allowing "a protein which binds to a GlcN residue in NAH or a derivative thereof (namely, the de-N-acetylated GlcNAc residue)" to contact with the solid phase of the present invention. Also, it is preferable that the "protein" which binds to a GlcN residue in NAH or a derivative thereof is an antibody. Additionally, it is preferable that the antibody which binds to a GlcN residue in NAH or a derivative thereof is a monoclonal antibody JM403.

The present invention also provides a kit for detecting ND activity in a sample, which comprises at least the following composing components (A) and (B) (to be referred to as "ND detection kit of the present invention" hereinafter):
(A) a polysaccharide of the present invention
(B) a protein which binds to a GlcN residue in NAH or a derivative thereof (namely, the de-N-acetylated GlcNAc residue).

It is preferable that the polysaccharide of the present invention is adhered to a solid phase. Also, it is preferable that "protein" which binds to a GlcN residue in NAH or a derivative thereof is an antibody. Additionally, it is preferable that the antibody which binds to a GlcN residue in NAH or a derivative thereof is a monoclonal antibody JM403.

The present invention also provides a method for detecting ST activity in a sample, which comprises at least the following steps (c) and (d) (to be referred to as "ST detection method of the present invention" hereinafter):

step (c): a step for allowing a sample and a sulfate group donor to contact with the solid phase of the present invention and step (d): a step for detecting N-sulfation in the polysaccharide of the present invention adhered to the aforementioned solid phase.

It is preferable that the detection of N-sulfation is carried out by allowing "a protein which binds to an N-sulfated GlcN residue in NAH or a derivative thereof" to contact with the solid phase of the present invention. Also, it is preferable that the "protein" which binds to an N-sulfated GlcN residue in NAH or a derivative thereof is an antibody. Additionally, it is preferable that the antibody which binds to an N-sulfated GlcN residue in NAH or a derivative thereof is a monoclonal antibody F58-10E4 or a monoclonal antibody HepSS-1. Particularly, the monoclonal antibody F58-10E4 can be preferably used.

The present invention also provides a kit for detecting ST activity in a sample, which comprises at least the following composing components (A) and (C) (to be referred to as "ST detection kit of the present invention" hereinafter):
(A) a polysaccharide of the present invention
(C) a protein which binds to an N-sulfated GlcN residue in NAH or a derivative thereof.

It is preferable that the polysaccharide of the present invention is adhered to a solid phase. Also, it is preferable that the "protein" which binds to an N-sulfated GlcN residue in NAH or a derivative thereof is an antibody. Additionally, it is preferable that the antibody which binds to an N-sulfated GlcN residue in NAH or a derivative thereof is a monoclonal antibody F58-10E4 or a monoclonal antibody HepSS-1. Particularly, the monoclonal antibody F58-10E4 can be preferably used.

The present invention also provides a method for detecting NDST activity in a sample, in which ND activity in the sample is detected by the ND detection method of the present invention and ST activity in the sample is also detected by the ST detection method of the present invention (to be referred to as "NDST detection method of the present invention" hereinafter).

The present invention also provides a kit for detecting NDST activity in a sample, which comprises at least the following composing components (A), (B) and (C) (to be referred to as "NDST detection kit of the present invention" hereinafter):
(A) a polysaccharide of the present invention
(B) a protein which binds to a GlcN residue in NAH or a derivative thereof (namely, the de-N-acetylated GlcNAc residue)
(C) a protein which binds to an N-sulfated GlcN residue in NAH or a derivative thereof.

It is preferable that the polysaccharide of the present invention is adhered to a solid phase. Also, it is preferable that the "protein" which binds to a GlcN residue in NAH or a derivative thereof is an antibody, Additionally, it is preferable that the antibody which binds to a GlcN residue in NAH or a derivative thereof is a monoclonal antibody JM403.

Also, it is preferable that the "protein" which binds to an N-sulfated GlcN residue in NAH or a derivative thereof is an antibody. Additionally, it is preferable that the antibody which binds to an N-sulfated GlcN residue in NAH or a derivative thereof is a monoclonal antibody F58-10E4 or a monoclonal antibody HepSS-1. Particularly, the monoclonal antibody F58-10E4 can be preferably used.

The present invention also provides a method for screening a substance which changes activities of 1 or 2 or more enzymes selected from the following group of enzymes, which comprises at least the following steps (e) to (g), (to be referred to as "screening method of the present invention" hereinafter)

step (e): a step for allowing a substance to be tested having a possibility of changing activities of 1 or 2 or more enzymes selected from the following group of enzymes to coexist with said enzymes;

step (f): a step for detecting activities of the aforementioned enzymes by any one of the ND detection method of the present invention, the ST detection method of the present invention and the NDST detection method of the present invention using the "mixture of the aforementioned substance to be tested and aforementioned enzymes" obtained by the step (e) as a sample; and step (g): a step for selecting a substance to be tested which changes activities of 1 or 2 or more enzymes selected from the following group of enzymes, by comparing the activities of enzymes detected by the step (f) with the activities of enzymes detected by the same method of step (f) using the enzymes used in the step (e) as the sample.
(group of enzymes): ND, ST and NDST.

Effect of the Invention

The polysaccharide of the present invention can be used as a raw material of the solid phase of the present invention and therefore is markedly useful. The solid phase of the present invention can be used in the various detection methods and various detection kits of the present invention and therefore is markedly useful. Each of the ND detection method of the present invention, ST detection method of the present invention and NDST detection method of the present invention can quantitatively and reproducibly detect ND activity, ST activity or NDST activity conveniently, quickly and specifically with high sensitivity and high accuracy at a moderate price and therefore is markedly useful. Also, each of the ND detection kit of the present invention, ST detection kit of the present invention and NDST detection kit of the present invention enable to carry out the aforementioned detection methods more conveniently and quickly and therefore is markedly useful. Also, the screening method of the present invention can screen a substance which changes the activity of ND, ST or NDST conveniently and quickly with high sensitivity and high accuracy at a moderate price and therefore is markedly useful. Additionally, the present invention can also be applied to the detection of diseases caused by the abnormal activities of NDST and the like enzymes, detection of risks thereof, understanding of morbid states and the like. Therefore it is markedly useful.

BEST MODE FOR CARRYING OUT THE INVENTION

Figure 1:
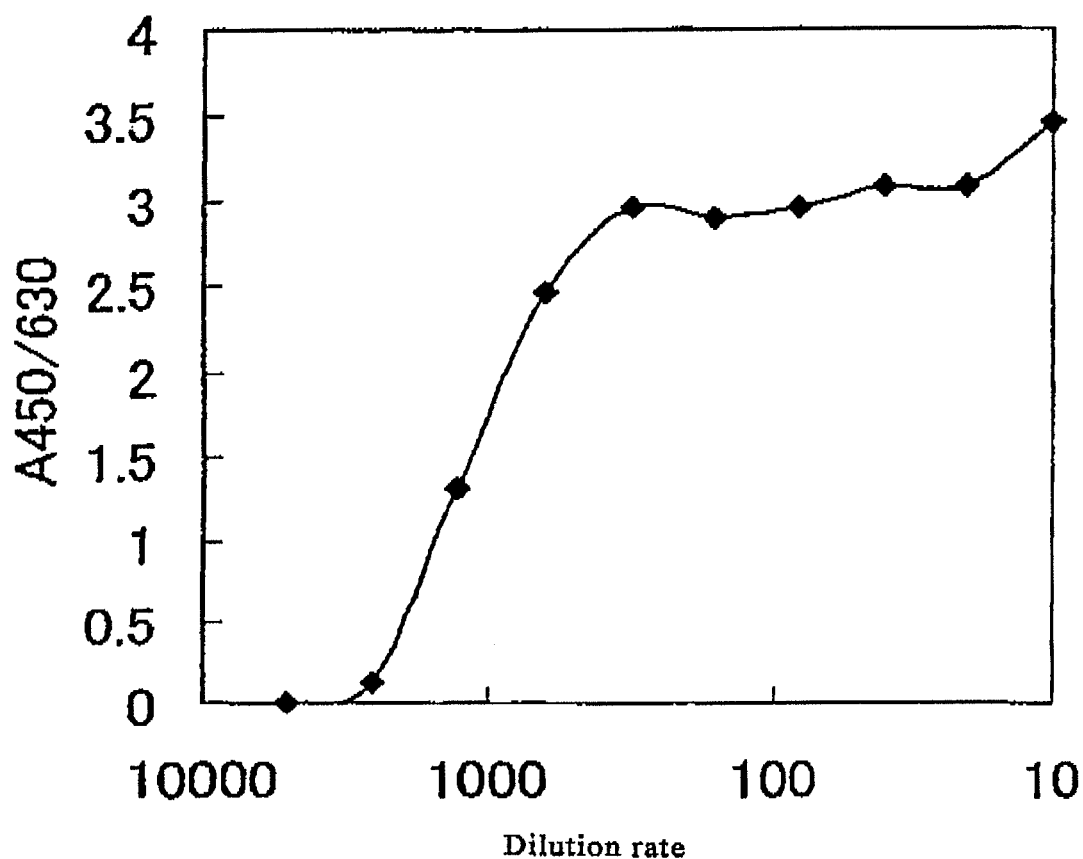
FIG. 1 shows dose-dependency of ND activity in the case where a NAH-SS-BSA-adhered plate is used.

The following describes the present invention in detail based on the best mode for carrying out the present invention.
<1> Polysaccharide of the Present Invention The polysaccharide of the present invention is a modified polysaccharide characterized in that a substance selected from the following group is bound to NAH or a derivative thereof.
(Group) Protein, Biotin and Antigenic Substance Though the "protein" as used herein is not particularly limited, it is preferably a soluble protein having a molecular weight of from 15,000 to 200,000, more preferably a soluble protein having a molecular weight of from 15,000 to 100,000, further preferably a soluble protein having a molecular weight of from 15,000 to 70,000. In this case, the "soluble" means that the protein can be dissolved in water, a physiological salts solution (physiological saline or the like), a buffer liquid and the like aqueous media at room temperature. Examples of the soluble protein having a molecular weight of from 15,000 to 200,000 include immunoglobulin, avidin, protein A, protein G, albumin and casein. Also, examples of the soluble protein having a molecular weight of from 15,000 to 100,000 or a molecular weight of from 15,000 to 70,000 include avidin, protein A, protein G, albumin and casein. Particularly, albumin or casein is preferable.

Examples of the "albumin" include serum albumin or egg albumin.

Additionally, the "NAH" as used herein is not particularly limited as long as it is recognized as NAH in this technical field, NAH is a polysaccharide in which GlcA residue and GlcNAc residue are alternately glycoside-bound. The linkage between GlcA residue and GlcNAc residue is β1,4 glycoside bond, and the linkage between GlcNAc residue and GlcA residue is α1,4 glycoside bond, As the general formula of NAH, it can be represented by the following (1) or (2),

(4GlcA β1-4GlcNAc α1)n    (1)

(4GlcNAc α1-4GlcA β1)n    (2)

(In the formulae, n represents an optional integer.)

As the NAH to be used as a material of the polysaccharide of the present invention, a conventionally known substance can be used. Its origin is not particularly limited too, and it may for example be a substance derived from a natural resource or an enzymatically or chemically synthesized substance, Examples of the substance derived from a natural resource include those which are derived from NAH-producing bacteria. As such bacteria, certain species of *Escherichia coli* and bacteria belonging to the genus *Pasturella* can be cited. For example, an *Escherichia coli* strain K5 and *Pasturella multosida* can be used. NAH can be produced for example by the method described in JP-A-2004-18840.

Additionally, the "derivative of NAH" according to the application documents means all of those in which certain modifications are made, such as those which maintain the sugar chain back born of NAH but also maintain other functional group or, on the contrary, those in which a functional group that should be originally maintained by the sugar chain back born of NAH is lost. Accordingly, all of those in which sulfate group is maintained on NAH, acetyl group is released from NAH, uronic acid forms epimer and the like are included in the general idea of "derivative of NAH", though not limited thereto. Additionally, the term "derivative of NAH" as used in the application documents is a general idea which includes not only those which are obtained by using NAH as a raw material and modifying this but also those which are obtained without using NAH as a raw material.

As the "derivative of NAH", a substance selected from the group consisting of the following (1) to (3) is preferable.
(1) N-desulfated HP or N-desulfated/N-acetylated HP
(2) N-desulfated HS or N-desulfated/N-acetylated HS
(3) de-N-acetylated NAH In this case, the "N-desulfated HP" means an HP in which the sulfate group bound to the 2-position amino group of the GlcN residue of HP is desulfated, and the "N-desulfated/N-acetylated HP" means an HP in which the sulfate group bound to the 2-position amino group of the GlcN residue of HP is desulfated and then the 2-position amino group of the GlcN group is acetylated, Also, the "N-desulfated HS" means an HS in which the sulfate group bound to the 2-position amino group of the GlcN residue of HS is desulfated, and the "N-desulfated/N-acetylated HS" means an HS in which the sulfate group bound to the 2-position amino group of the GlcN residue of HS is desulfated and then the 2-position amino group of the GlcN group is acetylated. Additionally, the "de-N-acetylated NAH" means an NAH in which the GlcNAc residue of NAH is de-N-acetylated. The "N-desulfated HP", "N-desulfated HS", "N-desulfated/N-acetylated HP" and "N-desulfated/N-acetylated HS" can be produced in accordance with the method described in JP-A-2003-113090 using HP or HS as the materials. Also, the "de-N-acetylated NAH" can be chemically produced using NAH as the material, in accordance with the method of Leali, D. et al. (*J. Biol. Chem.*, 276, 41, 37900-37908 (2001)), the method of Shaklee, P. K. et al (*Biochem. J.*, 217, 187-497 (1984)) or the like. Additionally, it can also be enzymatically produced by allowing human NDST prepared in accordance with the method of Aikawa, J. et al. (*J. Biol. Chem.*, 274 (5), 2690-2695 (1999)) or the like to react upon NAH.

Weight average molecular weight of the NAH or a derivative thereof which can be used as a material of the polysaccharide of the present invention is not particularly limited too, and though it can change based on the presence or absence of sulfate group, acetyl group and the like, the presence or absence of the addition of other compound and the like, for example, those having from 1,500 to 500,000 is preferable, those having from 4,000 to 200,000 is more preferable, those having from 10,000 to 200,000 is more preferable, those having from 20,000 to 150,000 is more preferable, those having from 20,000 to 100,000 is more preferable, and those having from 20,000 to 80,000 is further preferable, when converted as the weight average molecular weight of purely the NAH sugar chain alone by excluding influences of sulfate group and the like and addition of other compound.

The polysaccharide of the present invention has a characteristic in that a substance selected from the aforementioned group is bound to such an NAH or a derivative thereof. Mode of the "bond" as used herein is not particularly limited as long as it is a bonding having such a strength or more that the substance selected from the aforementioned group and NAH or a derivative thereof are not dissociated in an aqueous solution. As such a bonding, for example, a covalent bond which is formed by 2 atoms holding several electrons in common, an affinity bond which is formed by the affinity between 2 molecules and the like can be used. When the substance selected from the aforementioned group is a protein, SS bond, aminoalkyl bond, amido bond and the like can be used as the covalent bond. Also, when the substance selected from the aforementioned group is a protein, biotin-avidin bond (bond between biotin and avidin) can be used as the affinity bond. In this connection, as a matter of course, streptoavidin is also included in the term "avidin" as used in the application documents.

Regarding the method for forming such bonds, conventionally known methods can be employed.

Also, when the substance selected from the aforementioned group is biotin, a biotinylated derivative of NAH or a derivative thereof can be produced in accordance, for example, with the method of Osmond, R. I. W. et al. (*Anal. Biochem.*, 310, 199-207 (2002)). According to this method, biotin can be covalently bound to the reducing end of the NAH or a derivative thereof.

Additionally, when the substance selected from the aforementioned group is an antigenic substance, the way of effecting its bonding to the NAH or a derivative thereof can be selected in response to the kind of the antigenic substance. For example, when the antigenic substance is a peptide, the same method of the aforementioned method for binding a protein can be employed. In this connection, the "antigenic substance" as used in the application documents means a substance which can produce an antibody for this when this is used as an immunogen (a substance which becomes an antigen).

The polysaccharide of the present invention may be produced by producing an NAH having a desired structure or a derivative thereof and then binding this with a substance selected from the aforementioned group, or by allowing a polysaccharide as the material of a desired NAH or a derivative thereof to bind in advance to a substance selected from the aforementioned group, and then modifying its sugar chain moiety into a desired structure by the aforementioned various sugar chain modification methods and the like.

Additionally, such a polysaccharide of the present invention may be further bound with other substance. For example, regarding a polysaccharide of the present invention in which an immunoglobulin is bound to an NAH or a derivative thereof, it may be bound to protein A or protein G via said immunoglobulin moiety, or regarding a polysaccharide of the present invention in which protein A or protein G is bound to an NAH or a derivative thereof, it may be bound to an immunoglobulin via said protein A or protein G moiety. Also, regarding a polysaccharide of the present invention in which avidin is bound to an NAH or a derivative thereof, it may be bound to biotin via said avidin moiety, or regarding a polysaccharide of the present invention in which biotin is bound to an NAH or a derivative thereof, it may be bound to abidin via said biotin moiety. Additionally, regarding a polysaccharide of the present invention in which an antigenic substance is bound to an NAH or a derivative thereof, it may be bound to an antibody for this via said antigenic substance moiety, or regarding a polysaccharide of the present invention in which an antibody is bound to an NAH or a derivative thereof, it may be bound to an antigenic substance via said antibody moiety. The substances obtained in this manner are also included in the polysaccharide of the present invention.

Regarding the aforementioned method for forming a covalent bond, conventionally known methods can be employed. Example of the method for covalently bonding a protein with an NAH is shown in the following, though not limited thereto.

Exemplification (1): A PDP-modified NAH is obtained by adding SPDP to a reductively aminated NAH using sodium cyanoborohydride or the like, and SH-NAH is obtained by adding dithiothreitol or the like to this. On the other hand, a PDP-modified protein is obtained by adding SPDP to a protein. Subsequently, a conjugation reaction is carried out by allowing both of them to contact with each other (both of them are bound to each other when the PDP-modified protein is reduced by the SH-NAH acting as a reducing agent), thereby carrying out a method in which a protein is covalently bound to the reducing end of NAH. The covalent bond formed by this is SS bond.

Exemplification (2): A method in which carboxyl group of a protein and amino group introduced into the reducing end of NAH are covalently bound by adding EDC to the "reductively aminated NAH using sodium cyanoborohydride or the like" and the protein and carrying out a conjugation reaction (both of them are bound by EDC acting as an activator). The covalent bond formed by this is amido bond.

Exemplification (3): A method in which formyl group of the reducing end of NAH and amino group of a protein are allowed to undergo the reaction to form Schiff base and then covalently bonding by reducing it using reducing agent such as trimethylamineborane. The covalent bond formed by this is aminoalkyl bond (—$CH_2$—NH—).

Exemplification (4): A method in which the reducing end of NAH is reduced and then free formyl group is introduced by periodic acid oxidation, and this is allowed to undergo the reaction with amino group of a protein to undergo the reaction to form Schiff base and then covalently bonding by reducing it using reducing agent such as trimethylamineborane. The covalent bond formed by this is aminoalkyl bond (—$CH_2$—NH—).

Exemplification (5): A method in which NAH and amino group of a protein are covalently bound using benzoquinone or the like.

Additionally, conventionally known methods can be employed as the aforementioned method for forming affinity bond. Example of the method for carrying out affinity bonding of a protein with NAH is shown in the following, though not limited thereto.

Exemplification (6): A method in which biotin is bound to the amino group moieties formed on the reducing end of NAH by reductive amination using sodium cyanoborohydride or the like or to the carboxyl group moieties of NAH. On the other hand, avidin is bound to a protein to form an affinity bond (biotin-avidin bond) through contacting them one another.

Exemplification (7): A method in which NAH is bound with avidin by any one of the methods of Exemplification (1) to Exemplification (5). A method in which, as occasion demands, biotin is bound to an amino group or carboxyl group moiety of a protein by further allowing a biotin derivative (Pierce Chemical Company) which specifically binds to amino group or carboxyl group to react with the protein to bind to the protein, and then an affinity bond (biotin-avidin bond) is effected by allowing this to contact with the avidin-bound NAH.

Exemplification (8): A method in which NAH is bound to various antigenic substances (e.g., an antigenic peptide (e.g. vaccine) and the like) by any one of the methods of Exemplification (1) to Exemplification (5). Next, an affinity bond (antigen-antibody bond) is effected by allowing this to contact with an antibody for this antigenic substance.

Exemplification (9): A method in which NAH is bound to various antigens (e.g., anti-BSA antibody and the like) by any one of the methods of Exemplification (1) to Exemplification (5). Also, as occasion demands, an affinity bond (antigen-antibody bond) is effected by allowing this to contact with an antigen protein for this antigenic substance.

Exemplification (10); A method in which NAH is bound to protein A (or protein G) by any one of the methods of Exemplification (1) to Exemplification (5). Also, as occasion demands, an affinity bond (protein A (or protein G)-immunoglobulin bond) is effected by allowing this to contact with an immunoglobulin (IgG or the like).

Exemplification (11): A method in which NAH is bound with an immunoglobulin (IgG or the like) by any one of the methods of Exemplification (1) to Exemplification (5). Also, as occasion demands, an affinity bond (protein A (or protein G)-immunoglobulin bond) is effected by allowing this to contact with protein A (protein G).

Additionally, it is preferable that the "bond" in the polysaccharide of the present invention is formed between a substance selected from the aforementioned group and the reducing end of NAH or a derivative thereof.

By binding a substance selected from the aforementioned group with NAH or a derivative thereof by these methods and the like, a modified polysaccharide (polysaccharide of the present invention) characterized in that the substance selected from the aforementioned group is bound to NAH or a derivative thereof can be produced.

<2> Solid Phase of the Present Invention

The solid phase of the present invention is a solid phase to which the polysaccharide of the present invention is adhered. The polysaccharide of the present invention is as described in the foregoing.

The solid phase to which the polysaccharide of the present invention is adhered is not particularly limited as long as it can adhere the polysaccharide of the present invention and is insoluble in water, samples and reaction liquids. As the shape of the solid phase, a plate (e.g., wells of a microplate or the like), a tube, beads, a membrane, a gel, a particulate solid phase carrier (for example, synthetic particle such as gelatin particle, kaolin particle, latex particle) and the like can be exemplified. Particularly, a microplate is preferable from the viewpoint of accurate quantitativeness and convenience for use.

As the material of the solid phase, polystyrene, polypropylene, polyvinyl chloride, nitrocellulose, nylon, polyacrylamide, polyallomer, polyethylene, glass, agarose and the like can be exemplified, Particularly among them, a plate of polystyrene as its material is desirable.

As the method for adhering the polysaccharide of the present invention to the surface of such a solid phase, general methods such as a physical adhesion method, an affinity bond method, a covalent bond method, an inclusion method (e.g., see Koteika Koso (Immobilized Enzymes), 1975, published by Kodansha, pp. 9-75) can be applied.

Among them, the physical adhesion method is preferable because the operation is convenient and frequently used.

Additionally, by adhering a substance having affinity for the substance selected from the aforementioned group (being contained in the molecule of the polysaccharide of the present invention) to a solid phase in advance, the polysaccharide of the present invention may be adhered to the solid phase via this. For example, when an immunoglobulin is bound to the polysaccharide of the present invention, the polysaccharide of the present invention can also be adhered to a solid phase via protein A (or protein G) adhered to the solid phase when an immunoglobulin is bound to the polysaccharide of the present invention, via an immunoglobulin adhered to the solid phase when protein A (or protein G) is bound to the polysaccharide of the present invention, via biotin adhered to the solid phase when avidin is bound to the polysaccharide of the present invention, via avidin adhered to the solid phase when biotin is bound to the polysaccharide of the present invention, via an antibody for an antigenic substance adhered to the solid phase when said antigenic substance is bound to the polysaccharide of the present invention, or via an antigenic substance (antigen of an antibody) adhered to the solid phase when said antibody is bound to the polysaccharide of the present invention, respectively.

As an example of the illustrative method of physical adhesion of the polysaccharide of the present invention or "a substance having affinity for the substance selected from the aforementioned group" to a solid phase, for example, a method can be used in which a buffer solution (a buffer liquid of approximately pH 7 to 9 (e.g., phosphate buffer, PBS, carbonate buffer or the like)) for the polysaccharide of the present invention or "a substance having affinity for the substance selected from the aforementioned group" is contacted to the solid phase and allowed to stand still at about 0° C. to 10° C., preferably about 0° C. to 5° C., for about 6 hours to 24 hours, preferably about 10 hours to 20 hours. When "a substance having affinity for the substance selected from the aforementioned group" is contacted to the solid phase, the polysaccharide of the present invention is added thereafter to form an affinity bond with said substance. Consequently, the solid phase of the present invention to which the polysaccharide of the present invention is adhered can be obtained.

Also, as occasion demands, the surface of the solid phase may be washed thereafter with a washing liquid. This washing is not particularly limited as long as it is carried out under such a condition that the polysaccharide of the present invention adhered to the solid phase does not dissociate. As the washing liquid, a buffer liquid (e.g., Tris buffer, phosphate buffer, PBS or the like) can be used.

Also, as occasion demands, it is preferable after this to cover portions where the polysaccharide of the present invention is not adhered, by allowing a blocking substance to contact with the solid phase. Examples of such a blocking substance include BSA, gelatin, casein, skim milk, AppleDuo (trade name, mfd. by Seikagaku Corporation) and the like. These may be used as a single component or as two or more components. Examples of the illustrative method of blocking include, a method in which a solution of AppleDuo (trade name, mfd. by Seikagaku Corporation) is allowed to contact to the solid phase and to stand still at about 0° C. to 37° C., preferably about 10° C. to 30° C., for about 30 minutes to 2 hours. As occasion demands, antiseptics and the like may be coexisted in the blocking solution.

Additionally, as occasion demands, this may be washed thereafter with the aforementioned washing liquid in order to remove the blocking substance and the like. Also, the plate may be dried after this at approximately from 10° C. to 37° C., <3> ND Detection Method of the Present Invention The ND detection method of the present invention is a method for detecting ND activity in a sample, which comprises at least the following steps (a) and (b)

step (a): a step for allowing a sample to contact with the solid phase of the present invention and step (b): a step for detecting de-N-acetylation in the polysaccharide of the present invention adhered to the aforementioned solid phase.

In this connection, the term "detection" as used in the application documents means to find out its objective substance as a certain form. Accordingly, the term "detection" as used in the application documents is a general idea of not only finding out existence (presence or absence) of its detection object but also finding out the detection object quantitatively (measuring the detection object quantitatively).

The following describes each of the steps.

1. Step (a)

The step (a) is a step for allowing a sample to contact with the solid phase of the present invention. The solid phase of the present invention is as described in the foregoing.

The "sample" as used herein may be a substance which contains an enzyme having ND activity or has a possibility of containing the same. Also, it is not necessary that treatments such as isolation or purification are applied in advance to this enzyme having ND activity in a sample. That is, even when enzymes other than the enzyme having ND activity, other protein components and the like are contained in the sample, the ND activity can be specifically detected according to the ND detection method of the present invention.

Additionally, the method for contacting the solid phase and a sample is not particularly limited as long as molecule of the polysaccharide of the present invention adhered to said solid phase and molecule of an enzyme having ND activity presenting in the sample are contacted to each other. For example, the sample may be added to the solid phase to contact with the same, solid phase may be added to the sample to contact with the same, or both of them may be simultaneously added to other container. The contacting method is not limited thereto and can be optionally decided by those skilled in the art according to shapes, materials and the like of the solid phase.

After allowing both of them to contact with each other, it is preferable to incubate them in order to effect sufficient reaction of molecule of the polysaccharide of the present invention adhered to said solid phase with molecule of the enzyme having ND activity presenting in the sample.

The incubation temperature is not particularly limited as long as it is a temperature at which the enzyme reaction is occurred, and room temperature can be used as an example thereof. Although time for incubation is not particularly limited too as long as it is enough for the sufficient reaction of the both of the substances, for example, from about 15 to 120 minutes is preferable, from about 30 to 60 minutes is more preferable.

After the reaction, the solid phase and liquid phase are separated. As occasion demands, it is preferable to wash the surface of the solid phase with a washing liquid. This washing is not particularly limited as long as it is carried out under such a condition that the polysaccharide of the present invention adhered to the solid phase does not dissociate. Examples of the washing liquid include a buffer liquid which contains a nonionic surfactant such as Tween series or the like (e.g., Tris-HCl buffer, phosphate buffer, PBS or the like).

When the solid phase of the present invention and a sample are contacted with each other, an enzyme having ND activity presenting in the sample acts upon the polysaccharide of the present invention adhered to the solid phase, and two or more of the GlcNAc residues existing in the molecule (sugar chain moiety) of said polysaccharide are de-N-acetylated. When ND activity of the enzyme presenting in the sample becomes high, correspondingly increased number of the GlcNAc residues existing in the molecule (sugar chain moiety) of the polysaccharide of the present invention adhered to the solid phase are de-N-acetylated.

2. Step (b)

The step (b) is a step for detecting de-N-acetylation in the polysaccharide of the present invention adhered to the aforementioned solid phase.

When the enzyme presenting in the sample keeps ND activity, the GlcNAc residues existing in the molecule (sugar chain moiety) of the polysaccharide of the present invention adhered to the solid phase by the step (a) are de-N-acetylated. Also, when ND activity of the enzyme presenting in the sample becomes high, correspondingly increased number of the GlcNAc residues are de-N-acetylated. In the step (b), the ND activity presenting in the sample is detected by detecting de-N-acetylation in the polysaccharide of the present invention adhered to the solid phase via the step (a).

Detection method of the de-N-acetylation in the polysaccharide of the present invention adhered to the solid phase is not particularly limited too, and it can be carried out for example by a physicochemical method (e.g., a chromatography method or the like), a chemical method (e.g., an amino group detection method) a biological method (e.g., a method making use of a biological affinity such as an immunoassay method) and the like. Particularly from the point of view including convenience and quickness, it is preferable to carry it out by a method which utilizes a biological affinity.

When the de-N-acetylation is detected by a biological affinity, it can be carried out by allowing "a protein which binds to the GlcN residue of NAH or a derivative thereof (that is, de-N-acetylated GlcNAc residue)" to contact with the solid phase of the present invention. It is preferable that such a protein is an antibody.

Accordingly, it is preferable that such a detection is carried out by an immunoassay. Examples of the immunoassay include ELISA, RIA and the like, and each of them can be used.

Not only an antibody itself but a fragment of the antibody keeping its antigen binding region (Fab) is included in the general idea of the "antibody" to be used herein. Also, the "antibody" to be used herein may be either a polyclonal antibody or a monoclonal antibody, but a monoclonal antibody is preferable from the points of view including specificity, uniformity, reproducibility, and mass and permanent productivity.

A monoclonal antibody JM403 can be used herein, for example. The monoclonal antibody JM403 can be produced by the method described in Kidney, Int., 41, p. 115 (1992). Additionally, since the monoclonal antibody JM403 is available from Seikagaku Corporation, this can also be used.

The method of "contact" in this case is as described in the step (a).

Additionally, after allowing both of them to contact with each other, it is preferable to incubate them in order to effect sufficient binding by the biological affinity. The incubation temperature is not particularly limited as long as it is a temperature at which the binding by biological affinity is generated. It may from about 2° C. to 37° C., more preferably, from about 4° C. to 25° C. The incubation time is not particularly limited as long as the aforementioned two undergo the reaction sufficiently, it may from about 0.5 to 2 hours, more preferably from about 1 to 1.5 hours.

After the reaction, the solid phase and liquid phase are separated. As occasion demands, it is preferable to wash the surface of the solid phase with a washing liquid. The point of this washing is the same as the point of the washing after enzyme reaction in the step (a).

In order to facilitate the detection, the "protein which binds to the GlcN residue of NAH or a derivative thereof (that is, de-N-acetylated GlcNAc residue)" may be already labeled with a label or will be labeled later. Although the label which can be used in the labeling is not particularly limited as long as it can be used in the general protein labeling, for example, an enzyme (e.g., peroxidase, alkaline phosphatase, β-galactosidase, luciferase, acetylcholinesterase, glucose oxidase or the like), a radioisotope ($^{125}$I, $^{131}$I, $^{3}$H or the like), a fluorescence dye (fluorescein isothiocyanate (FITC), 7-amino-4-methylcoumarin-3-acetic acid (AMCA), dichlorotriazinylaminofluorescein (DTAF), tetramethylrhodamine isothiocyanate (TRITC), Lissamine Rhodamine, Texas Red, Phycoerythrin (PE), umbelliferone, europium, phycocyanin, tricolor, cyanin or the like), a chemiluminescent substance (luminol or the like), a hapten (dinitrofluorobenzene, adenosine monophosphate (AMP), 2,4-dinitroaniline or the like) and either one substance of a specific binding pair (biotin and avidins (streptoavidin or the like), lectin and a sugar chain, an agonist and a receptor of the agonist, HP and antithrombin III (ATIII) or the like) can be used.

Additionally, after binding the "protein which binds to the GlcN residue of NAH or a derivative thereof (that is, de-N-acetylated GlcNAc residue)" to the GlcN residue of the polysaccharide of the present invention adhered to the solid phase, it way be detected by further using a second protein (a secondary antibody or the like) which binds to said protein. It is preferable that this second protein (a antibody or the like) is labeled in advance with the aforementioned label.

By detecting the label linked to such a "protein which binds to the GlcN residue of NAH or a derivative thereof (that is, de-N-acetylated GlcNAc residue)" or the second protein (a secondary antibody or the like) linked thereto, de-N-acetylation of the GlcNAc residue of the polysaccharide of the present invention adhered to the solid phase can be detected.

Regarding the method for detecting a label, a conventionally known detection means can be optionally selected according to the kind of the label. For example, when one of a specific binding pair (e.g., biotin) is used as the label, the specific binding pair is formed by adding an enzyme (e.g., peroxidase or the like) linked by the other substance which specifically binds to this (e.g., streptoavidin). Subsequently, the label can be detected by adding a substrate of said enzyme (e.g., hydrogen peroxide (when the enzyme is peroxidase)) and a color developer (e.g., TV, diaminobenzidine or the like) and measuring coloring degree of the product by the enzyme reaction through its absorbance.

Additionally, when a radioisotope, a fluorescence dye or a chemiluminescent substance is used as the label for example, methods for measuring radioactivity count, fluorescence intensity, fluorescence polarization, luminescence intensity and the like can be used.

De-N-acetylation of the GlcNAc residue of the polysaccharide of the present invention adhered to the solid phase can be detected via the detection of such a label, and accordingly the ND activity in a sample can be detected. When many labels were detected, it means that the degree of de-N-acetylation is proportionally high, namely the ND activity in the sample is high.

When qualitative detection of ND activity (detection of the existence (presence or absence) of the ND activity) is desired, presence or absence of the detection of label can be regarded directly as the detection result. Also, when quantitative detection of ND activity (degree of the ND activity, measurement of concentration of an enzyme having ND activity or the like) is desired, absorbance, radioactivity count, fluorescence intensity, luminescence intensity or the like can be directly used as the index of the amount of the ND activity. Additionally, concentration of an enzyme having the ND activity in a sample can also be calculated by preparing a calibration curve or relational expression in advance using a standard solution of known concentration of the enzyme having the ND activity, and by using this.

<4> ND Detection Kit of the Present Invention

The ND detection kit of the present invention is a kit for detecting ND activity in a sample, which comprises at least the following composing components (A) and (B):
(A) a polysaccharide of the present invention
(B) a protein which binds to a GlcN residue in NAH or a derivative thereof (namely, the de-N-acetylated GlcNAc residue).

Regarding the polysaccharide of the present invention, it is as described in the foregoing. The polysaccharide of the present invention may be adhered to a solid phase at the timing of use or adhered to the solid phase in advance, but the one adhered to the solid phase in advance is preferable.

Additionally, regarding the "protein which binds to the GlcN residue of NAH or a derivative thereof (that is, de-N-acetylated GlcNAc residue)", it is also as described in the foregoing. Accordingly, examples of such protein include an antibody, and examples of such antibody include the monoclonal antibody JM403.

The ND detection kit of the present invention can be used in accordance with the ND detection method of the present invention. A standard article of known concentration of an enzyme having the ND activity to be used as the standard of a calibration curve or relational expression, a label detecting reagent and the like can be further added to the ND detection kit of the present invention as its constitutions, as long as ND detection kit of the present invention comprises at least the aforementioned composing components. Additionally, the aforementioned blocking substance, aforementioned washing liquid, a reaction stopping liquid and the like may be contained therein in addition to these constitutions. Additionally, a positive control (QC control) can also be contained in the ND detection kit of the present invention for the purpose of keeping the practice level among detection batches at a constant level.

These composing components can be preserved as a kit which can be used in accordance with the ND detection method of the present invention at the timing of use, for example by storing them in respectively separated containers.

<5> ST Detection Method of the Present Invention

The ST detection method of the present invention is a method for detecting ST activity in a sample, which comprises at least the following steps (c) and (d):

step (c); a step for allowing the solid phase of the present invention to contact with a sample and a sulfate group donor and step (d): a step for detecting N-sulfation in the polysaccharide of the present invention adhered to the aforementioned solid phase.

Regarding explanation of the ST detection method of the present invention, the same explanation is applied when the "ND" in the aforementioned ND detection method of the present invention is replaced by "ST", and the "de-N-acetylation" in the same is replaced by "N-sulfation", the "GlcNAc residues" in the same is replaced by "GlcN residues", the "protein which binds to the GlcN residue of NAH or a derivative thereof" in the same is replaced by "protein which binds to the N-sulfated GlcN residue of NAH or a derivative thereof", and the "monoclonal antibody JM403" in the same is replaced by "monoclonal antibody F58-10E4 or monoclonal antibody HepSS-1", respectively. Particularly, the monoclonal antibody F58-10E4 can be suitably used. The monoclonal antibody F58-10E4 can be produced by the method described in *J. Cell Biol.*, 119, p. 961 (1992). Additionally, since the monoclonal antibody F58-10E4 and monoclonal antibody HepSS-1 are available from Seikagaku Corporation, they can also be used.

In this connection, according to the ST detection method of the present invention, it is necessary to use a "sulfate group donor". PAPS is preferable as the sulfate group donor which can be used herein, though not particularly limited as long as it is a substance having a capacity to give sulfate group to the polysaccharide of the present invention as the sulfate group acceptor.

<6> ST Detection Kit of the Present Invention

The ST detection kit of the present invention is a kit for detecting ST activity in a sample, which comprises at least the following composing components (A) and (C):
(A) a polysaccharide of the present invention
(C) a protein which binds to an N-sulfated GlcN residue in NAH or a derivative thereof.

The ST detection kit of the present invention can be used in accordance with the ST detection method of the present invention.

Regarding explanation of the ST detection kit of the present invention, the same explanation is applied when the "ND" in the aforementioned ND detection kit of the present invention is replaced by "ST", and the "protein which binds to the GlcN residue of NAH or a derivative thereof" in the same is replaced by "protein which binds to the N-sulfated GlcN residue of NAH or a derivative thereof", and the "monoclonal antibody JM403" in the same is replaced by "monoclonal antibody F58-10E4 or monoclonal antibody HepSS-1", respectively. Particularly, the monoclonal antibody F58-10E4 can be suitably used, Additionally, the ST detection kit of the present invention may further contain a sulfate group acceptor as a composing component. Explanation of the sulfate group acceptor is the same as the explanation in the aforementioned ST detection method of the present invention.

<7> NDST Detection Method of the Present Invention

The NDST detection method of the present invention is a method for detecting NDST activity in a sample, characterized in that ND activity in the sample is detected by the ND detection method of the present invention and ST activity in the sample is also detected by the ST detection method of the present invention.

When the ND detection method of the present invention and the ST detection method of the present invention are used in combination in this manner, the NDST activity having both of the ND activity and ST activity can be detected. The NDST detection method of the present invention comprises at least a step for carrying out the ND detection method of the present invention and ST detection method of the present invention and may further comprise other steps. Additionally, the order of carrying out the ND detection method of the present invention and ST detection method of the present invention in the NDST detection method of the present invention is not particularly limited too. That is, the former may be carried out firstly, the latter may be carried out firstly or these may be carried out simultaneously.

Accordingly, when ND activity was detected in a sample by the ND detection method of the present invention and ST activity was detected in the sample by the ST detection method of the present invention, it can be judged that the NDST activity is present in the sample. Also, when only one of these activity was detected, it can be judged that ND activity is present but ST activity is not present in the sample or ST activity is present but ND activity is not present.

Additionally, when the ND activity and ST activity are quantitatively detected, characteristics of the NDST activity presenting in the sample (e.g. said NDST has higher ST activity than ND activity, or said NDST has ST activity and ND activity at the same level) can also be detected.

<8> NDST Detection Kit of the Present Invention

The NDST detection kit of the present invention is a kit for detecting NDST activity in a sample, which comprises at least the following composing components (A), (B) and (C):
(A) a polysaccharide of the present invention
(B) a protein which binds to a GlcN residue in NAH or a derivative thereof (that is, the de-N-acetylated GlcNAc residue)
(C) a protein which binds to an N-sulfated GlcN residue in NAH or a derivative thereof.

Regarding the polysaccharide of the present invention, it is as described in the foregoing. The polysaccharide of the present invention may be adhered to a solid phase at the timing of use or adhered to the solid phase in advance, but the one adhered to the solid phase in advance is preferable.

Additionally, regarding the "protein which binds to the GlcN residue of NAH or a derivative thereof (that is, de-N-acetylated GlcNAc residue)", it is also as described in the foregoing. Accordingly, examples of such protein include an antibody, and examples of such antibody include the monoclonal antibody JM403.

Also, regarding the "protein which binds to the N-sulfated GlcN residue of NAH or a derivative thereof", it is also as described in the foregoing. Accordingly, examples of such protein include an antibody, and examples of an antibody include the monoclonal antibody F58-10E4 or monoclonal antibody HepSS-1. Particularly, the monoclonal antibody F58-10E4 can be suitably used.

Additionally, the ST detection kit of the present invention may further contain a sulfate group acceptor as a composing component. Explanation of the sulfate group acceptor is the same as the explanation in the aforementioned ST detection method of the present invention.

The NDST detection kit of the present invention can be used in accordance with the NDST detection method of the present invention.

A standard article of known concentration of an enzyme having the NDST activity to be used as the standard of a calibration curve or relational expression, a label detecting reagent and the like can be further added to the NDST detection kit of the present invention as its constitutions, as long as the NDST detection kit of the present invention comprises at least the aforementioned composing components. Additionally, the aforementioned blocking substance, aforementioned washing liquid, a reaction stopping liquid and the like may be contained therein in addition to these constitutions. Additionally, a positive control (QC control) can also be contained in the ND detection kit of the present invention for the purpose of keeping the practice level among detection batches at a constant level.

These composing components can be preserved as a kit which can be used in accordance with the NDST detection method of the present invention at the timing of use, for example by storing them in respective separate containers.

<9> Screening Method of the Present Invention

The screening method of the present invention is a method for screening a substance which changes activities of 1 or 2 or more enzymes selected from the following group of enzymes, which comprises at least the following steps (e) to (g):

step (e): a step for allowing a substance to be tested having a possibility of changing activities of 1 or 2 or more enzymes selected from the following group of enzymes to coexist with said enzymes;

step (f): a step for detecting activities of the aforementioned enzymes by any one of the ND detection method of the present invention, the ST detection method of the present invention and the NDST detection method of the present invention using the "mixture of the aforementioned substance to be tested and aforementioned enzymes" obtained by the step (e) as a sample;

step (g): a step for selecting a substance to be tested which changes activities of 1 or 2 or more enzymes selected from the following group of enzymes, by comparing the activities of enzymes detected by the step (f) with the activities of enzymes detected by the same method of step (f) using the enzymes used in the step (e) as the sample.

(Group of Enzymes): ND, ST and NDST.

In the screening method of the present invention, the ND detection method of the present invention, the ST detection method of the present invention or the NDST detection method of the present invention is applied to the screening method of a substance which changes the activity of ND, ST or NDST.

The step (e) is a step for allowing a substance to be tested having a possibility of changing activities of these enzymes to coexist with said enzymes. The mode of this "coexistence" is not particularly limited as long as molecules of the substance to be tested having said possibility and molecules of said enzymes are under a condition where they can contact to each other. The enzyme which is allowed to coexist with the substance to be tested can be optionally selected by those skilled in the art according to the purpose of screening. For example, a substance having a possibility of changing ND activity is allowed to coexist with ND when screening of a substance which changes said activity is carried out, a substance having a possibility of changing ST activity is allowed to coexist with ST when screening of a substance which changes said activity is carried out or a substance having a possibility of changing NDST activity is allowed to coexist with NDST when screening of a substance which changes said activity is carried out.

In this connection, each of the ND, ST and NDST to be coexisted with a substance to be tested can be produced, for example, by the method described by Aikawa, J. et at. in *Journal of Biological Chemistry*, vol. 276, no. 8, p. 5876-5882, 2001. Kinds, origins and the like of the ND, ST and NDST to be coexisted to the substance to be tested can be optionally selected by those skilled in the art according to the purpose. For example, when human derived NDST is used, the enzyme to be used can be optionally selected from NDST 1, NDST 2, NDST 3, NDST 4 and the like according to the purpose. These enzymes can also be produced by conventionally known methods (e.g., see *Genomics*, 26(2), p, 239-244 (1995), *Biochem. J.*, 332(pt 2), p. 303-307 (1998), *J. Biol. Chem.*, 274(5), p. 2690-2695 (1999), *J. Biol. Chem.*, 276(8), p. 5876-5882 (2001) and the like). Additionally, an enzyme introduced with mutation such as substitution, deletion, insertion, rearrangement, an enzyme fused with other peptide or the like may be used, for example.

In this connection, when ST or NDST is selected as the enzyme, a sulfate group acceptor is also coexisted. Explanation of the sulfate group acceptor is the same as the explanation in the aforementioned ST detection method of the present invention.

The step (f) is a step for detecting activities of the aforementioned enzymes by any one of the ND detection method of the present invention, the ST detection method of the present invention and the NDST detection method of the present invention using the "mixture of the aforementioned substance to be tested and aforementioned enzymes" obtained by the step (e) as a sample. Employment of a suitable detection method can be optionally selected by those skilled in the art according to the purpose of screening. For example, the ND detection method of the present invention is employed when screening of a substance which changes ND activity is carried out, and the ST detection method of the present invention is used when screening of a substance which changes ST activity is carried out or the NDST detection method of the present invention is used when screening of a substance which changes NDST activity is carried out. Consequently, activity of the aforementioned enzyme in the presence of the aforementioned substance to be tested can be detected.

The step (g) is a step for selecting a substance to be tested which changes activities of 1 or 2 or more enzymes selected from the aforementioned group of enzymes, by comparing the activities of enzymes detected by the step (f) (activities of enzymes in the presence of a substance to be tested) with the activities of enzymes (activities of enzymes in the absence of a substance to be tested) detected by the same method of step (f) using the enzymes used in the step (e) as the sample. When a deference was found between the "activities of enzymes detected by the step (f) (activities of enzymes in the presence of a substance to be tested)" and "activities of enzymes (activities of enzymes in the absence of a substance to be tested) detected by the same method of step (f) using the enzymes used in the step (e) as the sample", said substance to be tested can be selected as the aforementioned substance which changes activity of the enzyme.

For example, when the activity of an enzyme in the presence of a substance to be tested is higher than the activity of the enzyme in the absence of the substance to be tested, said substance can be selected as an accelerator of the enzyme activity. Also, when the activity of an enzyme in the presence of a substance to be tested is lower than the activity of the enzyme in the absence of the substance to be tested, said substance can be selected as an inhibitor of the enzyme activity. When there is no difference between them, said substance can be identified as a substance which does not exert influence upon the enzyme activity.

Additionally, when a difference was found between the activity of an enzyme in the presence of a substance to be tested and the activity of the enzyme in the absence of the substance to be tested, degree of the difference may be quantitatively examined and used as an index of its ability as the accelerator or inhibitor of the enzyme activity.

EXAMPLES

The following more illustratively describes the present invention based on examples, but the present invention is not limited thereto.

In this connection, the NDST used in the examples was prepared in the following manner.

A human derived NDST 2 was cloned by the method described in *Biochem. J.*, 332(pt 2), p. 303-307 (1998). The DNA coding for the cloned NDST 2 has the nucleotide sequence described in SEQ ID NO:1 and encodes a protein (NDST 2) having the amino acid sequence described in SEQ ID NO:2.

The following operation was carried out in order to effect expression of a protein (NDST 2 from which the transmembrane region was deleted) consisting of an amino acid sequence shown by the amino acid numbers 79 to 883 in SEQ ID NO:2, by deleting a moiety coding for the N terminal side transmembrane region from the nucleotide sequence.

(1) Specific amplification of a DNA coding for a lobster L21 sequence (AACTCCTAAAAAACCGCCACC) (SEQ ID No.5) and a gp67 signal peptide (39 amino acids) was carried out by carrying out PCR having 1 cycle of 95° C. 2 minutes, 10 cycles of 95° C. 30 seconds-52.5° C. 30 seconds-72° C. 1 minute and 1 cycle of 72° C. 10 minutes using a thermal cycler, in a reaction system of 25 µl using 250 ng of a vector DNA pAcSecG2T (Pharmingen, U.S.A.) harboring a sequence coding for the baculovirus gp 67 signal peptide as the template and using 5 pmol of a short chain DNA having a sequence of 5'-GATCGGATCCAACTCCTAAAAAAC-CGCCACCATGCTCCTAGTAAATCAG-3' (SEQ ID NO:3) and 5 pmol of a short chain DNA having a sequence of 5'-CACGGGTTCAGTTCGACCTGTCTCCG-CAAAGGCAGAATGCGCCGC-3' (SEQ ID NO:4) and 1.25 units of Pyrobest (Takara, Japan) in the presence of 20 mM Tris-HCl (pH 8.3), 10 mM KCl, 6 mM $(NH_4)SO_4$, 2 mM $MgSO_4$, 0.1% Triton X-100, 0.001% BSA and 200 µM dNTP.

(2) Specific amplification of a DNA coding for 805 amino acids (amino acid numbers 79 to 883 in SEQ ID NO:2) of human NDST 2 was carried out by carrying out PCR having 1 cycle of 95° C. 2 minutes, 20 cycles of 95° C. 30 seconds-52.5° C. 30 seconds-72° C. 5 minutes and 1 cycle of 72° C. 10 minutes using a thermal cycler, in a reaction system of 25 µl using 250 ng of a plasmid DNA pCRhNDST2#5 harboring human NDST 2 in a vector as the template and using 5 pmol of a short chain DNA having a sequence of 5'-GAGA-CAGCTCGAACTGAACCCGTGG-3' (SEQ ID NO:6), 5 pmol of a short chain DNA having a sequence of 5'-CTGG-TATGGCGGCCGCAATTGTCAGCCCA-GACTGGAATGCTGCAG TTC-3' (SEQ ID NO:7) and 1.25 units of Pyrobest (Takara, Japan) in the presence of 20 mM Tris-HCl (pH 8.3), 10 mM KCl, 6 mM $(NH_4)SO_4$, 2 mM $MgSO_4$, 0.1% Triton X-100, 0.001% BSA and 200 µM dNTP.

(3) Specific amplification of a fusion DNA coding for the lobster L21 sequence, the gp67 signal peptide (39 amino acids) and 805 amino acids (amino acid numbers 79 to 883 in SEQ ID NO:2) of human NDST 2 was carried out by carrying out PCR having 1 cycle of 95° C. 2 minutes, 30 cycles of 95° C. 30 seconds-52.5° C. 30 seconds-72° C. 6 minutes and 1 cycle of 72° C. 10 minutes using a thermal cycler, in a reaction system of 25 μl using the DNA in 2 μl of the reaction liquid obtained in the aforementioned (1) and 0.5 μl of the reaction liquid obtained in the aforementioned (2) as the template and using 5 pmol of a short chain DNA having a sequence of 5'-GATCGGATCCAACTCCTAAAAAACCGCCAC-3' (SEQ ID NO:8), 5 pmol of a short chain DNA having a sequence of 5'-CTGGTATGGCGGCCGCAATTGTCAGC-CCAGACTGGAATGCTGCAGTTC-3' (SEQ ID NO:7) and 1.25 units of Pyrobest (Takara, Japan) in the presence of 20 mM Tris-HCl (pH 8.3), 10 mM KCl, 6 mM (NH$_4$)SO$_4$, 2 mM MgSO$_4$, 0.1% Triton X-100, 0.001% BSA and 200 μM dNTP.

(4) Restriction enzymes BamHI and NotI in 10 units for each were added to 10 μl of the fusion DNA-containing reaction liquid obtained in the aforementioned (3) and 1 μg of a vector DNA pFastBac-1 (Invitrogen, U.S.A.) and allowed to undergo the reaction at 37° C. for 2 hours. The reaction products were subjected to a TAE agarose electrophoresis, and the DNA fragment of desired size was purified using Geneclean II Kit and recovered in 10 μl of TE buffer. Using 1 μl of each of the thus obtained DNA preparations, the fusion DNA coding for the lobster L21 sequence, gp67 signal peptide (39 amino acid) and human NDST2 805 amino acids (amino acid numbers 79 to 883 in SEQ ID NO:2), simultaneously digested with BamHI and NotI, was ligated with pFastBac-1 simultaneously digested with BamHI and NotI, in a reaction system of 4° C., 20 hours and 10 μl using DNA Ligation Kit ver. 2 (Takara, Japan). Using 2 μl of the reaction liquid, 40 μl of *Escherichia coli* DH5α competent cell (Invitrogen, U.S.A.) was transformed in the usual way, and colonies of the transformants were selected on the 1.5% agar containing LB medium containing 50 μg/ml ampicillin. Plasmid DNA possessed by the *E. coli* was recovered from the obtained *E. coli* colony in 100 μl of 10 mM Tris-HCl (pH 8.5). Analysis of the nucleotide sequences of DNA fragments inserted into the vector DNA was carried out in the usual way using a short chain DNA specific for the human NDST 2.

As a result, tow clones considered to be harboring the DNA fragment of interest (pFB1-GP67hNDST2SOL(79E)#5 and pFB1-GP67hNDST2SOL(79E)#123) were identified from a fragment of 2577 bp obtained by digesting with BamHI and NotI of the fusion DNA coding for the lobster L21 sequence, gp67 signal peptide (39 amino acid) and human NDST2 805 amino acids (amino acid numbers 79 to 883 in SEQ ID NO:2), and 128 *E. coli* clones transformed with the ligation product of pFastBac-1 digested with BamHI and NotI, By carrying out the nucleotide sequence analysis of DNA, it was confirmed that the aforementioned two clones completely coincide with the expected nucleotide sequence of DNA.

(5) The DNA obtained by the aforementioned (4) was transferred into *E. coli* DH10BAC (Invitrogen, U.S.A.) and, in accordance with the protocol of Invitrogen, colonies of the transformants were selected on the 1.5% agar-containing LB medium supplemented with 50 μg/ml kanamycin, 7 μg/ml gentamicin and 10 μg/ml tetracycline.

The thus obtained *E. coli* colony was inoculated into 1.5 ml of Terific-Broth medium (Beckton Dickinson, U.S.A.) containing 50 μg/ml kanamycin and cultured on a shaker at 37° C. for 20 hours. The thus obtained culture liquid was transferred into a 1.5 ml capacity Eppendorf tube and then centrifuged at 4° C. and at 8000 rpm for 2 minutes using a cooling centrifuge to recover *E. coli* cells as the precipitate. The cells were suspended in 150 μl of 50 mM Tris-HCl (pH 8.0) containing 10 mM EDTA and 100 μg/ml RNase A, followed by the addition of 150 μl of 200 mM NaOH containing 1% (w/v) SDS, and then gently mixed and allowed to stand still at room temperature for 5 minutes. Next, 150 μl of 3.0 M potassium acetate (pH 5.5) was added thereto and thoroughly mixed, followed by centrifugation at 4° C. and at 15000 rpm for 10 minutes using a cooling centrifuge to recover the supernatant fraction. To 450 μl. of the supernatant, 450 μl of phenol (Invitrogen, U.S.A.) saturated in advance with TE buffer was added and vigorously mixed using Vortex mixer, followed by centrifugation at 4° C. and at 15000 rpm for 5 minutes using a cooling centrifuge to recover the supernatant fraction. To 400 μl of the supernatant fraction, 1 ml of ethanol was added and mixed, followed by 10 minutes of standing at room temperature. Thereafter, the supernatant was removed by 5 minutes of centrifugation at 4° C. and at 15000 rpm using a cooling centrifuge and then, after adding 1 ml of 70% (v/v) ethanol to the precipitate and subsequent mixing, the supernatant was removed by 5 minutes of centrifugation at 4° C. and at 15000 rpm using a cooling centrifuge. The remaining precipitate was suspended by adding 150 μl of 50 mM Tris-HCl (pH 8.0) containing 10 mM EDTA and 100 μg/ml RNase A and then allowed to undergo the reaction at 37° C. for 20 minutes. Next, 100 μl of phenol (Invitrogen, U.S.A.) saturated in advance with TE buffer was added thereto and vigorously mixed using Vortex mixer, followed by centrifugation at 4° C. and at 15000 rpm for 5 minutes using a cooling centrifuge to recover the supernatant fraction. After adding 250 μl of ethanol and 10 μl of 3 M sodium acetate to 100 μl of the supernatant fraction and subsequent mixing, the supernatant was removed by 5 minutes of centrifugation at 4° C. and at 15000 rpm using a cooling centrifuge. Next, 1 ml of 70% (v/v) ethanol was added to the precipitate and mixed, and then the supernatant was removed by 5 minutes of centrifugation at 4° C. and at 15000 rpm using a cooling centrifuge. The remained precipitate was suspended by adding 100 μl of TE buffer.

As a result, the clone of interest (pFB1-GP67hNDST2SOL (79E)#123-4) was obtained using drug resistance and PCR as the indexes, by transferring the DNA pFB1-GP67hNDST2SOL(79E)#123 obtained in the aforementioned (4) into *E. coli* DH10BAC.

(6) Firstly, 1,000,000 cells of a Barathra cell Sf9 were suspended in 2 ml of SF-900II serum-free medium (Invitrogen, U.S.A.) and then transferred to a 6 well plate and allowed to stand still at 28° C. for 1 hour to adhere the cells to the plate. Next, 10 μg of the DNA obtained in the aforementioned (5) (lobster L21 sequence, gp67 peptide and human NDST2 805 amino acids integrated into baculovirus genomic DNA) was diluted to 200 μl of the Sf-900II serum-free medium and mixed with 6 μl of cellfectin (Invitrogen, U.S.A.) which had been diluted to 200 μl of the Sf-900II serum-free medium, and allowed to stand still at room temperature for 30 minutes. After washing the Sf cells adhered to the plate in advance with 2 ml of Sf-900II serum-free medium, a mixture of 200 μl mixed liquid of the DNA and cellfectin with 800 μl of Sf-900II serum-free medium was added thereto. After standing still at 28° C. for 5 hours, the medium was removed by suction, 2 ml of new Sf-900II serum-free medium was added thereto, the culturing was further carried out at 28° C. for 3 days, and then the culture supernatant was recovered and used as a baculovirus stock liquid.

(7) Ten million cells of Sf21 cell were suspended in 10 ml of SF-900II (serum-containing medium) and then inoculated into a T-75 flask and allowed to stand still for 1 hour. The medium was removed by suction but leaving 2 ml and 1 ml of the baculovirus stock liquid obtained in the aforementioned (6) was added thereto and gently shaken, thereby infecting the S521 (serum-containing medium) with the virus stock liquid.

Thereafter, 8 ml of the SF-900II (serum-containing medium) was added thereto, followed by 3 days of culturing at 28° C.

(8) The recovered medium was centrifuged and the fraction from which the cells were removed was used as the culture supernatant. The culture supernatant was applied to Amicon Ultra-15 30000 MWCO (Millipore, U.S.A.), and a fraction of a molecular weight of 30,000 or more was recovered by centrifugation using a cooling centrifuge and used as a concentrated culture supernatant.

The thus obtained solution containing NDST2 (a protein consisting of an amino acid sequence shown by the amino acid numbers 79 to 883 in SEQ ID NO:2 (NDST2 from which the transmembrane region was removed)) is called "NDST enzyme liquid" hereinafter.

Example 1

Production of the Polysaccharide of the Present Invention (1) Production of NAH

NAH was produced using *E. coli* K5 in accordance with the method described in JP-A-2004-18840. Characteristics of the produced NAH are shown below.
- Weight average molecular weight (Mw) measured by a gel filtration chromatography: 44,710
- Number average molecular weight (Mn) measured by a gel filtration chromatography: 36,714
- Degree of molecular weight dispersion (Mw/Mn): 1.212
- The nucleic acid content measured by ethidium bromide (EtBr) colorimetry: 0.09%
- The protein content measured by the Lowry method (*J. Biol. Chem.*, 193, 265 (1951): 2.38%
- Mol value of free amine measured by 2,4,6-trinitrobenzene sulfonic acid (2,4,6-TNBS) method (*Biochimica et Biophysica Acta.*, 141, 358 (1967)): 0.026 µM/mg In this case, the gel filtration chromatography was carried out in accordance with the method of Arai, M. et al. (*Biochem. Biophys. Acta.*, 1117, 60-70, 1992). Weight average molecular weight and number average molecular weight were determined by using sodium chondroitin sulfate having known molecular weights (weight average molecular weight 39,100, 18,000, 8,050; all mfd. by Seikagaku Corporation) and sodium hyaluronate (weight average molecular weight 104,000; mfd. by Seikagaku Corporation) as the standard articles, analyzing their elution times of a gel filtration chromatography which used a high performance liquid chromatography by using a data analysis software (GPC-8020, TOSOH), and applying elution times of samples to the thus obtained formula. The column was used by connecting TSK gel G4000PWXL, G3000PWXL and G2500PWXL (φ 7.8×300 mm for each, TOSOH). As the solvent, 0.2 mol/l sodium chloride solution was used, the flow rate was set to 0.6 ml/min, and a differential refractometer (RI—8020), TOSOH) was used as the detector.

(2) Production of the Polysaccharide of the Present Invention in which a Protein (BSA) is Covalently Bound (SS Bond) to the Reducing End of NAH (2-1) Preparation of Thiopropionyl NAH (to be Referred to as "SH-NAH" Hereinafter)

50 mg of the NAH prepared in Example 1 was weighed and dissolved in 2 ml of 2 M ammonium chloride aqueous solution. To the solution, 25 mg of sodium cyanoborohydride was added to carry out reductive amination reaction at 70° C. for 2 days. To further carry out the reaction under the same condition for 2 days, 13 mg of sodium cyanoborohydride was added to the reaction mixture. After cooling on an ice bath, the reaction was completely terminated by adding 400 µl of acetic acid.

The thus formed reductively-aminated NAH (to be referred to as "RA-NAH" hereinafter) was recovered by a solvent precipitation method using 2 volumes of ethanol. The thus recovered precipitate was washed with ethanol and then lyophilized. Consequently, 39.5 mg of RA-NAH lyophilized preparation was obtained.

10.4 mg of the thus obtained RA-NAH was weighed and dissolved in 2 ml of 0.1 M sodium chloride-0.1 M phosphate buffer (pH 7.5). To the solution, 80 µl of 5 mM SPDP (SIGMA) (ethanol solution) was added to carry out a PDP modification reaction at room temperature for 30 minutes. Thereafter, in order to remove excess SPDP, this reaction liquid was dialyzed overnight against distilled water, followed by lyophilizing. Consequently, 9.5 mg of 2-pyridinylsulfidopropionylated NAH (to be referred to as "PDP-NAH" hereinafter) lyophilized preparation was obtained.

After weighing 9.5 mg of the thus obtained PDP-NAH, it was dissolved in 1 ml of 0.1 M sodium chloride-0.1 M sodium acetate buffer (pH 4.5). Dithiothreitol was added to this solution to a final concentration of 25 mM to carry out reduction reaction at room temperature for 60 minutes.

The thus formed SH-NAH was recovered by a solvent precipitation method using 2 volumes of ethanol. The thus recovered precipitate was washed with ethanol and then lyophilized. As a result, 8.3 mg of SH-NAH lyophilized preparation was obtained.

(2-2) Preparation of 2-pyridyldisulfidopropionylated BSA (to be Referred to as "PDP-BSA" Hereinafter)

BSA (100 mg, SIGMA) was dissolved in 0.1 M sodium chloride-0.1 M phosphate buffer (pH 7.5) to obtain a final concentration of 2.5 mg/ml. To the solution, 5 mM SPDP (ethanol solution) was added to obtain a final concentration of 238 µM, and then a PDP modification reaction was carried out at room temperature for 30 minutes. In order to remove excess SPDP, this reaction liquid was dialyzed overnight against distilled water, followed by lyophilizing. Consequently, 104.2 mg of 2-pyridyldisulfidopropionylated BSA (to be referred to as 'PDP-BSA' hereinafter) lyophilized preparation was obtained.

(2-3) Formation of Covalent Bond (SS Bond) (Preparation of the Polysaccharide of the Present Invention)

The SH-NAH (1.5 mg) and PDP-BSA (0.75 mg) prepared in the above were dissolved in 1 ml of 0.1 M sodium chloride-0.1 M phosphate buffer (pH 7.5) to carry out a conjugation reaction at room temperature for 2 hours. In order to remove pyridyl-2-thione generated through the reaction, the solution after the reaction was dialyzed overnight against distilled water, followed by lyophilizing. Consequently, 1.9 mg of the polysaccharide of the present invention in which a protein (BSA) is covalently bound (SS bond) to the reducing end of NAH (to be referred to as "NAH-SS-BSA" hereinafter) was obtained.

(3) Production of the Polysaccharide of the Present Invention in which Biotin is Bound to the Reducing End of NAH The RA-NAH (10 mg) obtained in the above was dissolved in 0.5 ml of 0.1 M sodium carbonate aqueous solution, subsequently adding 3 mg of sulfo-NHS-LC-biotin (mfd. by Pierce Chemical Company) thereto followed by overnight incubation at 4° C. After overnight dialysis against distilled water thereafter, the dialyzed liquid was lyophilized to obtain the polysaccharide of the present invention in which biotin is bound to the reducing end of NAH (to be referred to as "NAH-biotin" hereinafter) (8 mg).

Example 2

Production of the Solid Phase of the Present Invention (a Solid Phase to which NAH-SS-BSA was Adhered)

The NAH-SS-BSA produced in Example 1 was diluted with PBS(−) to 1 μg/ml. 100 μl of the solution after this dilution was added to each well of MaxiSorp (registered trademark) 96 well microplate (manufactured by NALGE NUNC) and allowed to stand still at 4° C. for 14 to is hours, thereby effecting uniform coating on the surface of the wells.

After washing this plate twice with PBS(−), a solution prepared by 5 times-diluted ApplieDuo (trade name, manufactured by Seikagaku Corporation) as a blocking substance and, as an antiseptic, a phosphate buffer containing 0.05% Proclin (registered trademark) 300 (manufactured by SUPELCO) (equivalent to the aforementioned PBS(−) which however does not contain sodium chloride and potassium chloride, pH 7.2 to 7.5; to be referred to as "PB" hereinafter) were respectively added thereto and allowed to stand still at room temperature for 2 hours.

After the standing, the plate in which the NAH-SS-BSA was adhered to its wells was obtained by sufficiently removing the blocking substance and drying it at 37° C. for 2 hours. The plate was stored in a refrigerator by sealing in an aluminum laminate bag together with a desiccant.

Example 3

Production of the Polysaccharide of the Present Invention in which a Protein (BSA) is Covalently Bound (Amido Bond) to the Carboxyl Group of NAH A solution containing NAH prepared in Example 1 and a solution containing BSA (mfd. by Serologicals Proteins) were respectively prepared to obtain a concentration of 10 mg/ml using 0.1 M MES buffer (pH 5.5) as the solvent. Also, a 100 mg/ml solution of EDC (mfd. by PIERCE) was prepared using 0.1 M MES buffer (pH 5.5) as the solvent.

The aforementioned NAH solution (300 μl) and BSA solution (150 μl) were mixed. After adding 4 μl of the EDC solution to the mixed liquid, a conjugation reaction was carried out at room temperature for 20 hours. The solution after the reaction was dialyzed overnight against distilled water and then lyophilized. Consequently, 3.5 mg of a lyophilized preparation of the polysaccharide of the present invention in which a protein (BSA) is covalently bound (amido bond) to the carboxyl group kept on the hexuronic acid residues of NAH (to be referred to as "NAH-COOH-BSA" hereinafter) was obtained.

Example 4

Production of the Solid Phase of the Present Invention (a Solid Phase to which NAH-COOH-BSA was Adhered)

Using "NAH-COOH-BSA" instead of the "NAH-SS-BSA" of Example 2, a plate in which NAH-COOH-BSA was adhered to its wells was obtained in the same manner as in Example 2. The plate was stored in a refrigerator by sealing it in an aluminum laminate bag together with a desiccant.

Example 5

Measurement of ND Activity

Each of the plates prepared in Examples 2 and 4 was washed three times with 300 μl of PBS(−) containing 0.05% polyoxyethylene (20) sorbitan monolaurate (a product which corresponds to the trademark Tween 20 of ICI; mfd. by Wako Pure Chemical Industries) (to be referred to as "washing liquid" hereinafter). Thereafter, an NDST enzyme liquid was serially diluted from 10 times to 5120 times using a solution containing 0.05 M MES, 10 mM $MnCl_2$ and 1% Triton X-100 (to be referred to as "enzyme reaction liquid 1" hereinafter) (pH 6.5), and 50 μl of the resulting solution was added to the wells in portions and allowed to stand still at 37° C. for 60 minutes to undergo the enzyme reaction.

After completion of the enzyme reaction, the wells were washed three times with the washing liquid. Thereafter, 100 μl of a solution of the monoclonal antibody JM403 (Seikagaku Corporation) adjusted to 1 μg/ml with 20 times-diluted solution of ApplieDuo (trade name; manufactured by Seikagaku Corporation) and PBS(−) containing 0.05% Proclin 300 (to be referred to as "reaction liquid" hereinafter) was added to the wells. Thereafter, the plate was allowed to stand still at ordinary temperature (15 to 25° C.) for 60 minutes to undergo the antigen-antibody reaction. A well containing the reaction liquid alone was used as the blank.

After the reaction, the wells were washed three times with the washing liquid, and 100 μl of a solution of an HRP-labeled goat anti-mouse immunoglobulin G+M antibody (mfd. by JACKSON) diluted 20,000 times with the reaction liquid was added to each well. Thereafter, the plate was allowed to stand still at ordinary temperature for 60 minutes to undergo the antigen-antibody reaction.

After the reaction, the plate was washed three times with the washing liquid, and 100 μl of a TMB solution (mfd. by BIOFX) was added to the each well as the substrate of peroxidase and allowed to undergo the reaction at ordinary temperature for 30 minutes to develop a color. Thereafter, the reaction was stopped by adding 100 μl of a reaction stopping liquid (mfd. by BIOFX) to each well and then the absorbance of the TMB degradation product at a wavelength of 450 nm (control wavelength 630 nm) was measured by a well reader SK 603 (registered trademark; available from Seikagaku Corporation).

The monoclonal antibody JM403 recognizes the GlcN residues moiety of NAH molecule (that is, de-N-acetylated GlcNAc residues). When the ND activity is high, the de-N-acetylated sites on the polysaccharide of the present invention adhered to the solid phase are proportionally increased, so that the degree of de-N-acetylation (ND activity) can be detected by detecting this de-N-acetylated moieties with the monoclonal antibody JM403. Accordingly, reactivity of the monoclonal antibody JM403 was expressed as the ND activity in this Example.

The ND activity was calculated as a value obtained by subtracting the absorbance of blank from the measured absorbance. A result in the case using a plate to which NAH-SS-BSA was adhered is shown in FIG. 1, and a result in the case using a plate to which NAH-COOH-BSA was adhered in FIG. 2.

Figure 2:
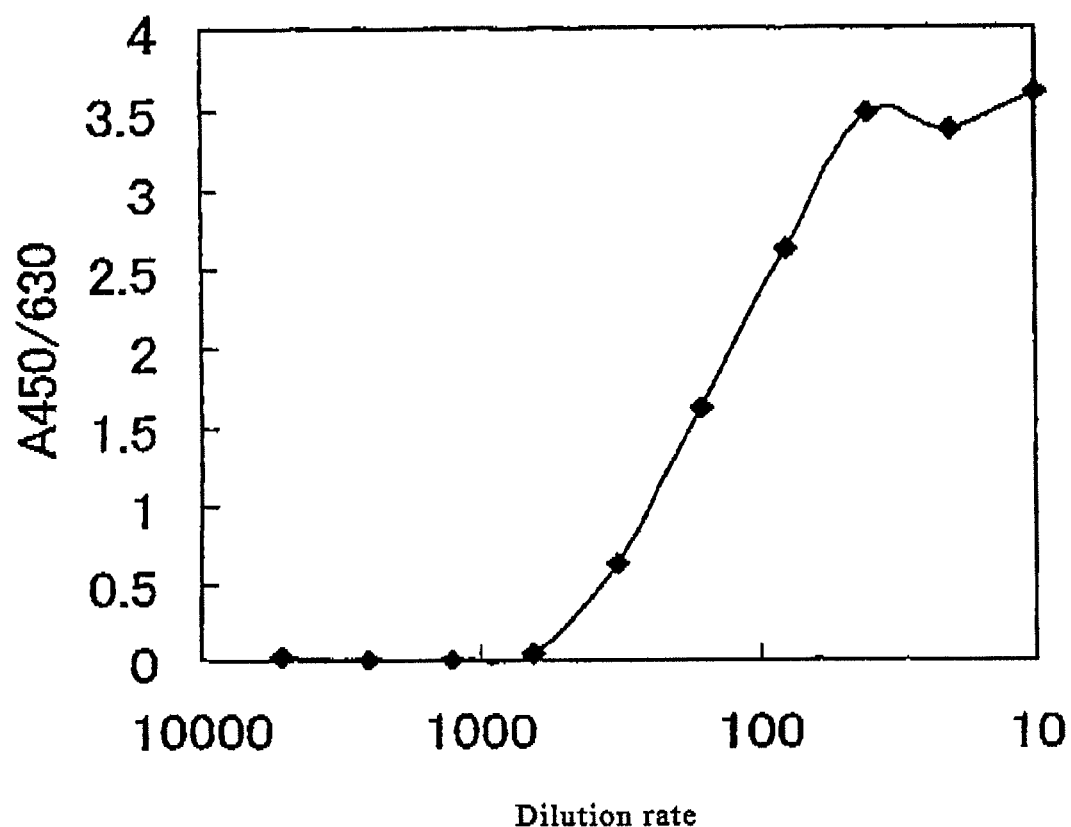
FIG. 2 shows dose-dependency of ND activity in the case where a NAH-COOH-BSA-adhered plate is used.

From FIG. 1 and FIG. 2, ND activity depending on the dose of NDST was observed in both cases (in inverse proportion to the dilution rate of the NDST enzyme liquid). Also, in the case of the plate to which the NAH-SS-BSA prepared by binding BSA to the reducing end of NAH was adhered, the ND activity was confirmed even using the 1280 times-diluted enzyme liquid (FIG. 1), so that it was able to measure the ND activity with higher sensitivity than the case of the plate to which the NAH-COOH-BSA was adhered (FIG. 2, the ND activity was confirmed by 320 times dilution rate).

Example 6

Dependency of ND Activity on Reaction Time

The plate prepared in Example 2 (NAH-SS-BSA-adhered plate) was washed three times with 300 μl of the washing liquid, and then 50 μl of the NDST enzyme liquid was diluted 160 times using the enzyme reaction liquid 1 and added to the each well. Thereafter, the enzyme reaction was effected by standing still at 37° C. for 0, 10, 20, 30, 40 or 60 minutes.

After completion of the reaction, 100 μl of a solution of the monoclonal antibody JM403 (Seikagaku Corporation) adjusted to 1 μg/ml with the reaction liquid was added to each well in. Thereafter, the plate was allowed to stand still at ordinary temperature (15 to 25° C.) for 60 minutes to undergo the antigen-antibody reaction. A well containing the reaction liquid alone was used as the blank.

In this connection, the test was carried in the same manner except that pH of the enzyme reaction liquid 1 was adjusted to 8.0 or the NDST enzyme liquid was boiled for 1 minute in advance and used instead of the NDST reaction liquid.

Figure 3:
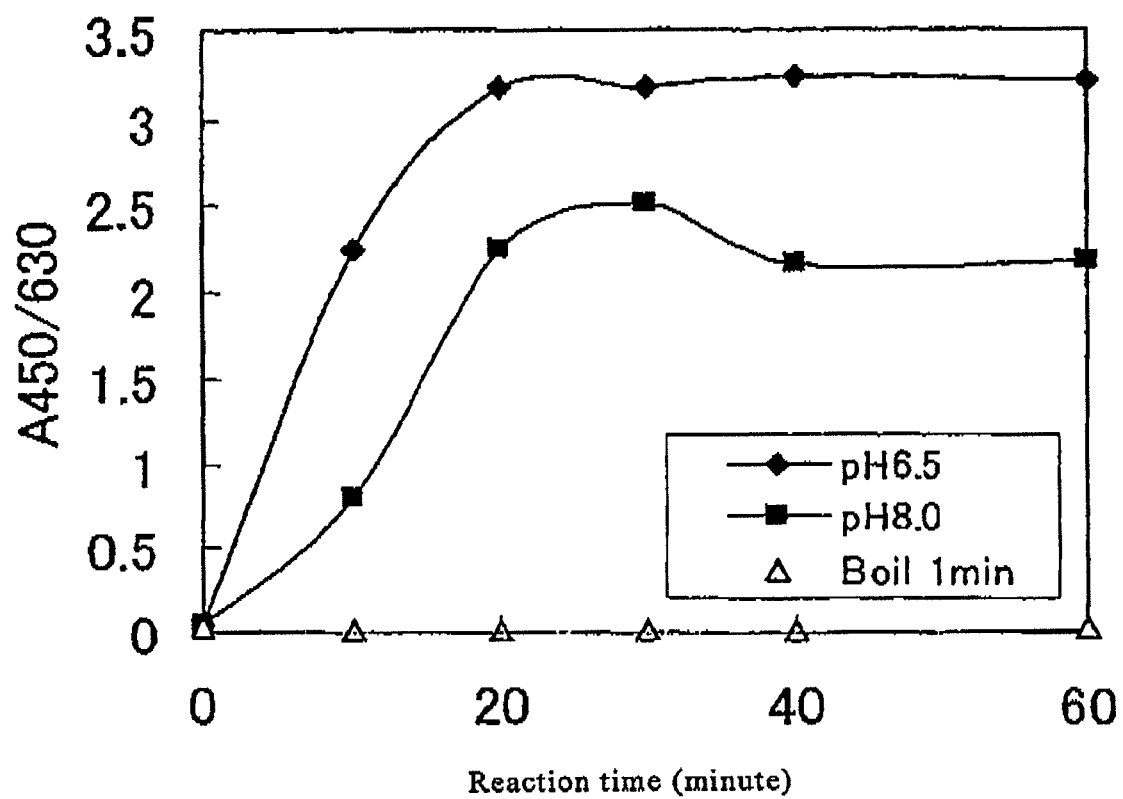
FIG. 3 shows reaction time-dependency of ND activity in the case where the NAH-SS-BSA-adhered plate is used.

Thereafter, the HRP-labeled goat anti-mouse immunoglobulin G+M antibody was allowed to undergo the reaction by the same method described in Example 5, and the ND activity was calculated by subsequently developing a color with the TMB solution and then measuring the absorbance. The results are shown in FIG. 3. In this connection, the black lozenge in FIG. 3 shows data of a test in which the enzyme reaction liquid 1 was used by changing its pH to 6.5, and the black square shows data of a test in which the enzyme reaction liquid 1 was used by changing its pH to 8.0, and the open triangle shows data of a test in which the NDST enzyme liquid boiled for 1 minute in advance was used.

From FIG. 3, when the enzyme reaction liquid 1 of pH 6.5 or pH 8.0 was used, the ND activity was found reaction time-dependently in both cases. Also, the enzyme reaction liquid 1 of pH 6.5 showed higher reactivity than the case using the enzyme reaction liquid 1 of pH 8.0. In this connection, it was confirmed that the ND activity is inactivated in the NDST enzyme liquid which was boiled for 1 minute. Accordingly, it was shown that it is preferable to adjust pH of the solution at the time of enzyme reaction to 6 to 7 when the ND activity is measured.

Example 7

Measurement of ST Activity

The plate prepared in Examples 2 (NAH-SS-BSA-adhered plate) was washed three times with 300 μl of the washing liquid.

Thereafter, the NDST enzyme liquid was serially diluted from 2 times to 128 times using a solution of pH 7.4 containing 50 mM HEPES, 1% Triton X-100, 1 mM MnCl$_2$, 10 mM MgCl$_2$ and 0.1 mM PAPS (to be referred to as "enzyme reaction liquid 2" hereinafter), and 50 μl of the resulting solution was added to each well and allowed to stand still at 37° C. for 30 minutes to undergo the enzyme reaction.

After completion of the enzyme reaction, the wells were washed three times with the washing liquid. Thereafter, a solution of the monoclonal antibody F58-10E4 (Seikagaku Corporation) was adjusted to 1 μg/ml with the reaction liquid, and 100 μl of the resulting solution was added to each well.

Thereafter, the plate was allowed to stand still at ordinary temperature (15 to 25° C.) for 60 minutes to undergo the antigen-antibody reaction. A well containing the reaction liquid alone was used as the blank.

In this connection, the case in which the enzyme reaction liquid2 containing no PAPS was used was also tested in the same manner. Thereafter, the HRP-labeled goat anti-mouse immunoglobulin G+M antibody was allowed to undergo the reaction by the same method described in Example 5, and the ST activity was calculated by subsequently developing a color with the TMB solution and then measuring the absorbance. The results are shown in FIG. 4.

Figure 4:
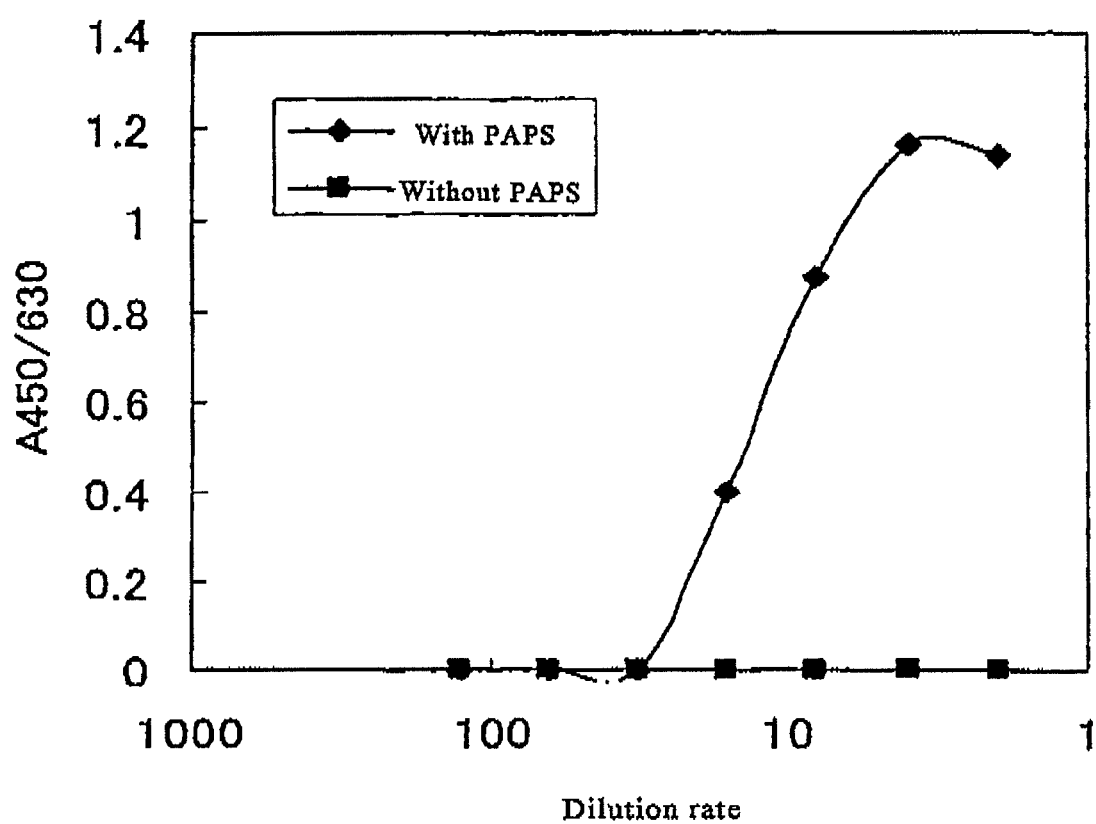
FIG. 4 shows dose-dependency and PAPS-dependency of ST activity (NDST activity) in the case where the NAH-SS-BSA-adhered plate is used.

From FIG. 4, ST activity depending on the dose of NDST was observed in both cases (in inverse proportion to the dilution rate of the NDST enzyme liquid). Additionally, since the ST activity was not detected in the absence of PAPS, it was confirmed that this enzyme reaction is a PAPS-dependent enzyme reaction.

Example 8

Dependency of ST Activity on Reaction Time

The plate prepared in Example 2 (NAH-SS-BSA-adhered plate) was washed three times with 300 μl of the washing liquid, and then the NDST enzyme liquid was diluted 8 times using the enzyme reaction liquid 2, and 50 μl of the resulting solution was added to the each well.

Thereafter, the enzyme reaction was effected by standing still at 37° C. for 0, 10, 20, 30, 40 or 60 minutes.

After completion of the reaction, the wells were washed three time with the washing liquid, and a solution of the monoclonal antibody F58-10E4 (Seikagaku Corporation) was adjusted to 1 μg/ml with the reaction liquid and 100 μl of the resulting solution was added to each well. Thereafter, the plate was allowed to stand still at ordinary temperature (15 to 25° C.) for 60 minutes to undergo the antigen-antibody reaction. A well containing the reaction liquid alone was used as the blank.

In this connection, the test was carried in the same manner except that the NDST enzyme liquid boiled for 1 minute in advance was used instead of the NDST reaction liquid.

Figure 5:
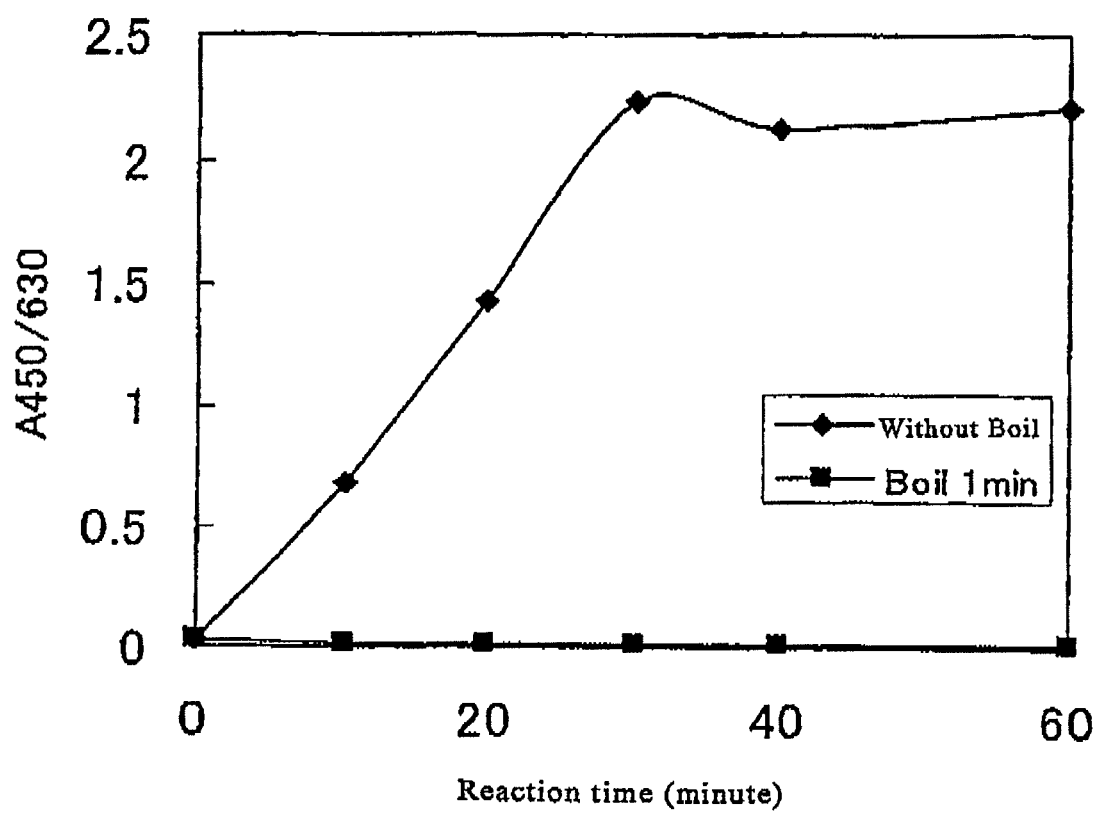
FIG. 5 shows reaction time-dependency and influence by heat treatment of ST activity (NDST activity) in the case where the NAH-SS-BSA-adhered plate is used.

Thereafter, the HRP-labeled goat anti-mouse immunoglobulin G+M antibody was allowed to undergo the reaction by the same method described in Example 5, and the ST activity was calculated by subsequently developing a color with the TMB solution and then measuring the absorbance. The results are shown in FIG. 5. In this connection, the black lozenge in FIG. 5 shows data of a test in which the NDST enzyme liquid not treated with boiling was used, and the black square shows data of a test in which the NDST enzyme liquid boiled for 1 minute in advance was used.

From FIG. 5, the reaction time-dependent ST activity was confirmed. In this connection, it was confirmed that the ST activity is inactivated in the case using the boiling of 1 minute due to thermal denaturation of the enzyme protein.

Also, though the ST activity is directly detected in Example 7, when it is taken into consideration that the NDST is an enzyme which causes N-sulfation after the induction of de-N-acetylation, it can be said that the detection of ST activity means that the de-N-acetylation occurred as its premise.

Accordingly, the detection of ST activity by this method can simultaneously detect the NDST activity including ND activity.

Additionally, detection of NDST activity can be carried out more precisely by detecting the ND activity in a sample by the ND detection method of the present invention and further detecting the ST activity in the sample by the ST detection method of the present invention.

Example 9

Production of the Solid Phase of the Present Invention (a Solid Phase to which NAH-Biotin was Adhered Via Avidin)

Streptoavidin (mfd. by Jackson) was diluted with PBS(−) to 20 μg/ml. 50 μl of the solution after this dilution was added to each well of MaxiSorp (registered trademark) 96 well microplate (mfd. by NALGE NUNC) and allowed to stand still at 4° C. for 14 to 18 hours, thereby effecting uniform coating on the surface of the wells.

After washing this plate twice with PBS(−), a solution prepared by 5 times-diluting AppleDuo (trade name, mfd. by Seikagaku Corporation) as a blocking substance and, as an antiseptic, the PB containing 0.05% Proclin (registered trademark) 300 (mfd. by SUPELCO) were respectively added thereto and allowed to stand still at room temperature for 2 hours.

After the standing, the plate in which streptoavidin was adhered to its wells (streptoavidin-adhered plate) was obtained by sufficiently removing the blocking substance and drying it at 37° C. for 2 hours.

This streptoavidin-adhered plate was washed three times with 300 μl of TBS containing 0.05% polyoxyethylene (20) sorbitan monolaurate (trademark of ICI, a product which corresponds to Tween 20; mfd. by Wako Pure Chemical Industries) (to be referred to as "T-TBS" hereinafter). Thereafter, the NAH-biotin produced in Example 1 was diluted to 1 μg/ml with TBS containing a 20 times-diluted solution of AppleDuo (trade name; manufactured by Seikagaku Corporation) and 0.05% Proclin 300, and 100 μl of the resulting solution was added to the each well and allowed to stand still at 37° C. for 30 minutes to undergo the reaction. After the reaction, the wells were washed three times with T-TBS, thereby producing the "solid phase to which NAH-biotin was adhered via avidin".

Example 10

Measurement of ND Activity

Figure 6:
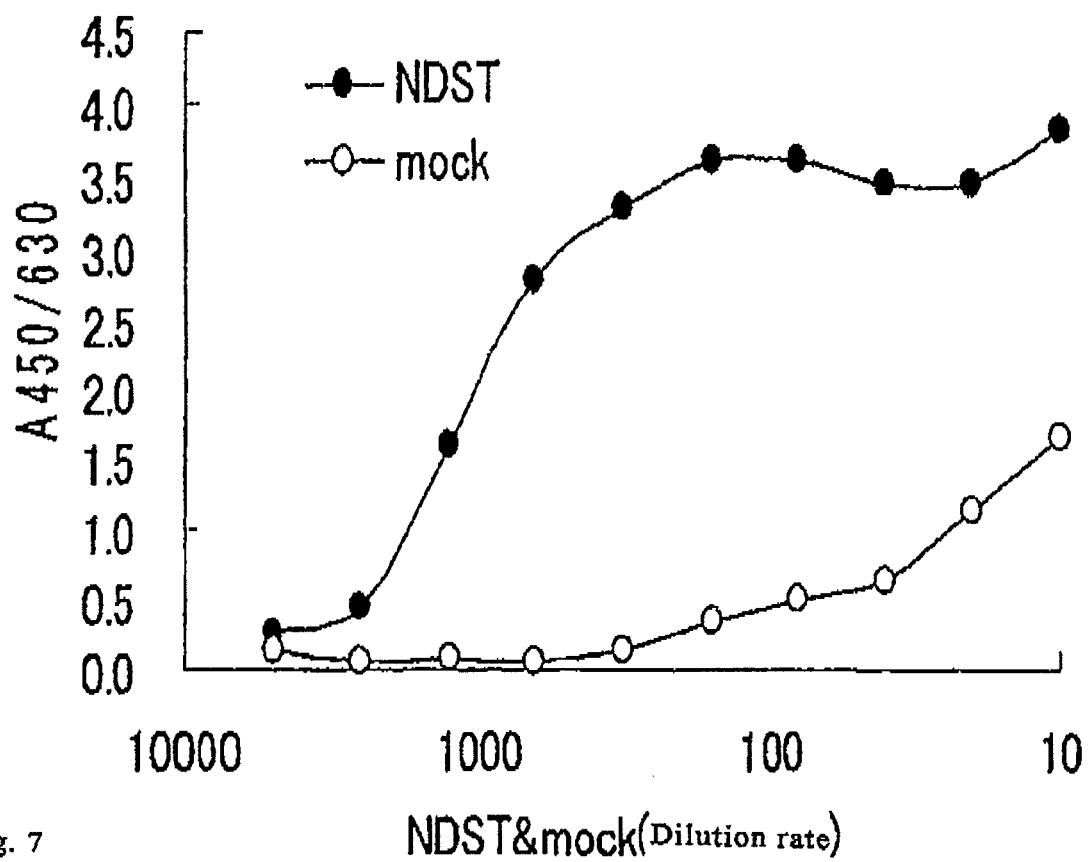
FIG. 6 shows dose-dependency of ND activity using a "plate to which NAH-biotin was adhered via avidin".

Using the plate produced in Example 9, ND activity of the NDST enzyme was measured in the same manner as in Example 5. In this connection, a culture supernatant obtained by infecting with only a baculovirus not integrated with the human NDST2 DNA was concentrated in the same manner as in the aforementioned Example 8 and used as a negative control (mock) in this Example. The mock was measured by diluting it in the same manner as the case of the NDST enzyme liquid. The results are shown in FIG. 6. In this connection, the black circle in FIG. 6 shows a result of the use of the NDST enzyme, and the open circle shows a result on mock, respectively.

From FIG. 6, ND activity depending on the dose of NDST was observed in both cases (in inverse proportion to the dilution rate of the NDST enzyme liquid). Also, in the case using this plate, it was able to confirm the ND activity even using the 1280 times-diluted enzyme liquid, so that it was able to measure the ND activity with high sensitivity. Additionally, it was shown that the ND activity can be measured more accurately, by calculating difference with the mock.

Example 11

Measurement of ST Activity

Figure 7:
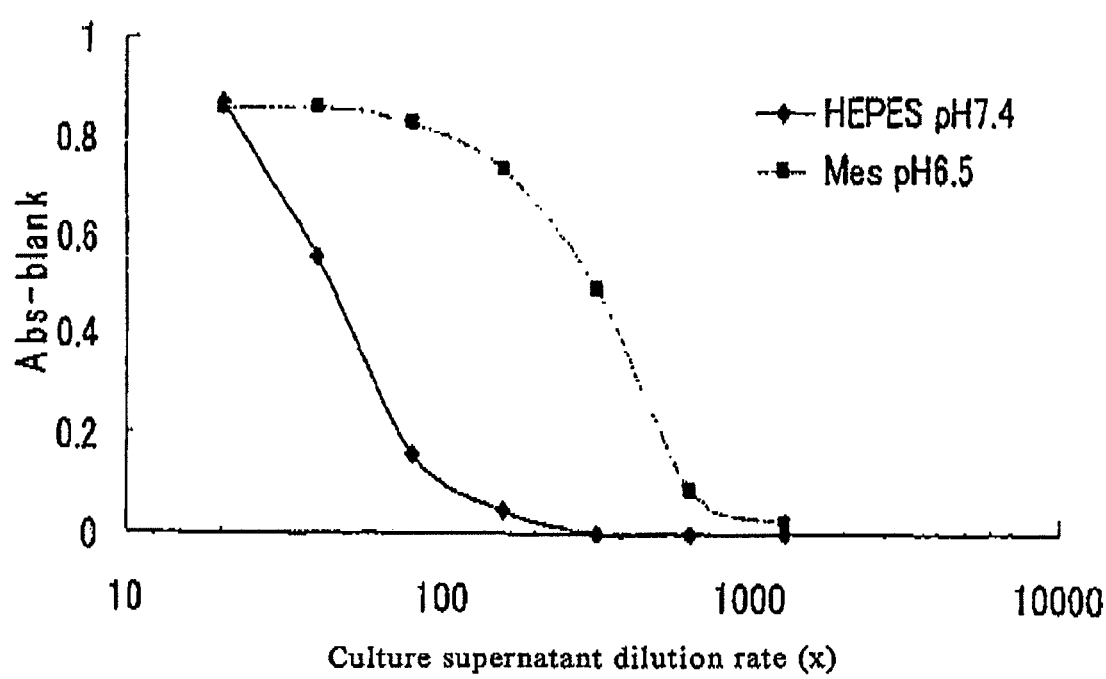
FIG. 7 shows influence of pH on the measurement of ND activity using the "plate to which NAH-biotin was adhered via avidin".

Using the plate produced in Example 9, ST activity of the NDST enzyme was measured in the same manner as in Example 7. In this connection, either one of the enzyme reaction liquid 2 and an enzyme liquid in which its pH was adjusted to 6.5 by using MES instead of the HEPES in the enzyme reaction liquid 2 was used in this Example. The results are shown in FIG. 7. In this connection, the lozenge in FIG. 7 shows a result in the case using the enzyme reaction liquid 2 (pH 7.4), and the square shows a result in the case using the enzyme reaction liquid adjusted to pH 6.5.

From FIG. 7, it was shown that the ST activity can be measured with higher sensitivity when the enzyme reaction liquid adjusted to pH 6.5 is used. Based on this, it was shown that it is preferable to adjust pH of the solution at the time of enzyme reaction to 6 to 7 when the ST activity is measured.

Example 12

Screening of a Substance which Exerts Influence Upon Enzyme Activity (ND Activity)

Each of the following 6 substances to be tested was diluted to 200, 20 or 2 μg/ml using the enzyme reaction liquid 1. Quickly after addition of 25 μl of the solutions to each well of the solid phase (plate) produced in Example 9, 25 μl of an "NDST enzyme liquid diluted 40 times with the enzyme reaction liquid I" was added to each well (final concentration of each substance to be tested 100, 10 or 1 μg/ml, final dilution rate of the enzyme liquid 80 times).

Figure 8:
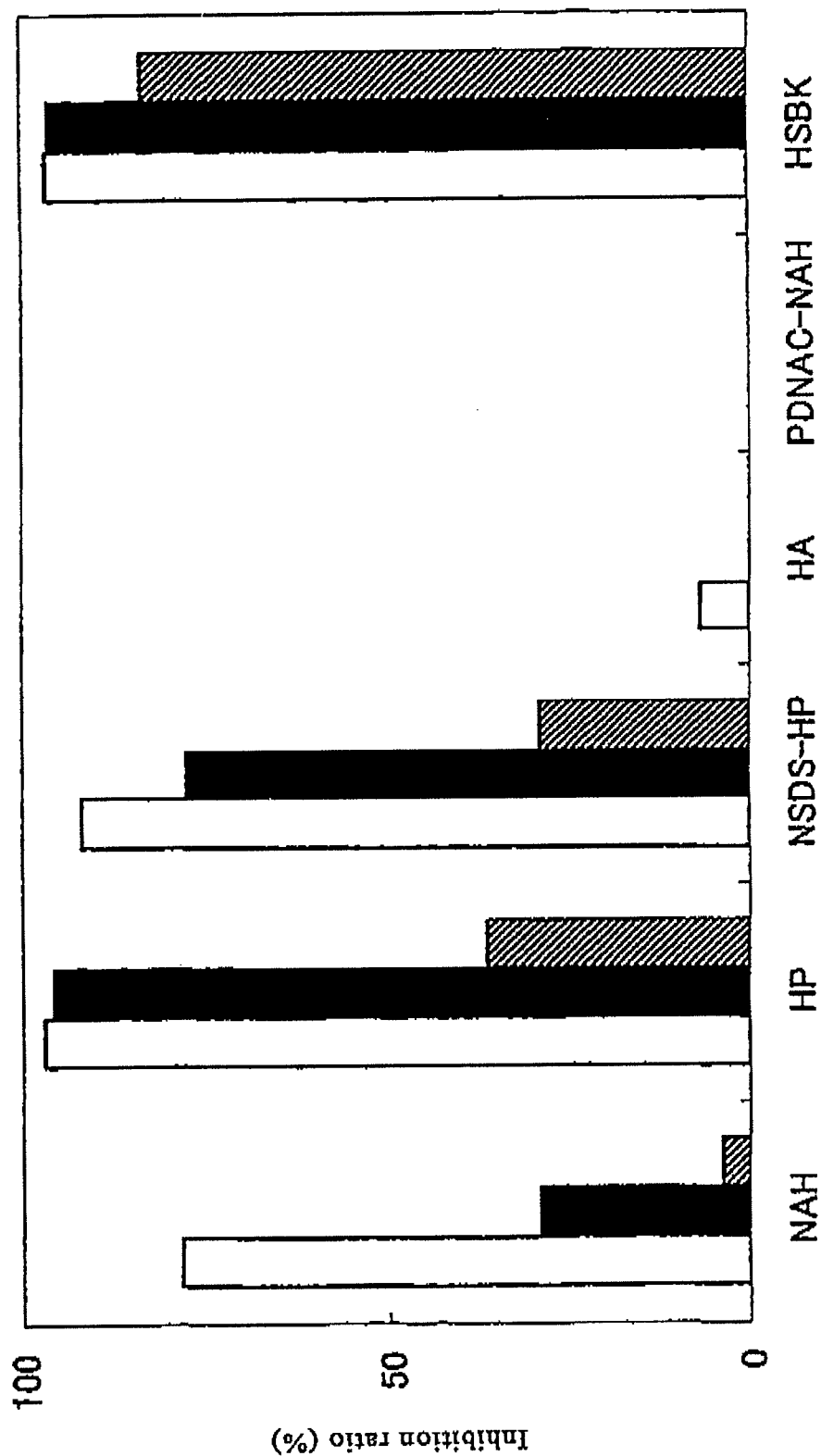
FIG. 8 shows a result of the screening of ND activity inhibitors using the "plate to which NAH-biotin was adhered via avidin".

Substance to be Tested (The Parentheses Show the Abbreviations in FIG. 8.)

NAH
Swine small intestine-derived HP (HP)
N-sulfated/completely de-O-sulfated HP (NSDS-HP)
Cockscomb-derived hyaluronic acid (weight average molecular weight 100 KDa; HA)
Partially de-N-acetylated NAH (PDNAC-NAH)
Bovine kidney-derived HS (HSBK)

Thereafter, the enzyme reaction was effected by standing still at 37° C. for 60 minutes. In this connection, the enzyme reaction liquid 1 alone was added to the wells to which the substances to be tested were not added.

After completion of the reaction, the wells were washed three times with T-TBS and 100 μl of a solution of the monoclonal antibody JM403 (Seikagaku Corporation) adjusted to 1 μg/ml with TBS was added to each well. Thereafter, the plate was allowed to stand still at ordinary temperature (15 to 25° C.) for 60 minutes to undergo the antigen-antibody reaction. After the reaction, the wells were washed three times with T-TBS, and 100 μl of the HRP-labeled goat anti-mouse immunoglobulin G+M antibody diluted 20000 times with TBS was added to each well. Thereafter, the plate was allowed to stand still at ordinary temperature for 60 minutes to undergo the antigen-antibody reaction.

After the reaction, this plate was washed three times with T-TBS, and 100 μl of the TMB solution was added to each well and allowed to undergo the reaction at ordinary temperature for 30 minutes to develop a color. Thereafter, the reaction was terminated by adding 100 µl of the reaction terminating liquid to each well, and then the absorbance was measured by the same method described in Example 5. Also, the rate of change (%) was calculated by the following calculation formula.

Rate of change(%)=100×((the value of absorbance when each substance to be tested is not added)−(the value of absorbance when each substance to be tested at respective concentration is added))/(the value of absorbance when each substance to be tested is not added).

In this connection, since the monoclonal antibody JM403 binds to the GlcN residues in NAH (that is, de-N-acetylated GlcNAc residue), higher value of the detected absorbance means that the number of GlcN residues in NAH is larger (that is, the number of de-N-acetylated GlcNAc residues is larger), namely the ND activity is higher. On the contrary, lower value of the detected absorbance means that the number of GlcN residues in NAH is smaller (that is, the number of de-N-acetylated GlcNAc residues is smaller), namely the ND activity is low.

Additionally, when a substance to be tested inhibits ND activity, the aforementioned rate of change (%) becomes a positive number. Also, higher value of the rate of change means higher ability of the substance to be tested to inhibit ND. The results are shown in FIG. 8. In this connection, the white column in FIG. 8 shows a result of a case wherein the final concentration of respective substance to be tested is 100 µg/ml, and the black column shows a result of a case wherein the same is 10 µg/ml and the shaded column shows a result of a case wherein the same is 1 µg/ml, respectively.

From FIG. 8, it was shown that NAH, HP, NSDS-HP and HSBK have the function to inhibit ND activity concentration-dependently. On the other hand, HA and PDNAC-NAH were hardly possessed of the function to inhibit ND activity.

From the above results, it was able to select NAH, HP, NSDS-HP and HSBK as substances which inhibit ND activity (ND inhibitors).

Additionally, among NAH, HP, NSDS-HP and HSBK, it was able to select HSBK as a substance having the highest ability to inhibit ND activity, followed by NSDS-HP, and it was able to select NAH a substance having the lowest ability to inhibit ND activity.

Example 13

Examination of Substrate for ST Activity Measurement

A polysaccharide in which biotin is bound to the reducing end of HSBK was prepared using HSBK instead of NAH and in accordance with the method described in Example 1(3). Next, this was adhered to a plate in accordance with the method described in Example 9.

Also, NAH was produced using the method described in Example 1(1) and de-N-acetylated heparosan was prepared by using this, and then various lots of N-sulfated heparosan was prepared by using this.

This de-N-acetylated heparosan can be prepared by a method which uses enzyme reactions of NDST2 and the like, or a method which uses chemical reactions. As the chemical de-acetylation method of glycosaminoglycan, the hydrazine degradation method (Patrick, N. and Conrad, H. E., *Bioche. J.*, 217, 187, (1984)) and the alkali hydrolysis method (Leali, G. et al., *J. Biol. Chem.*, 276, 37900 (2001)) are known, but the latter method was used here. Illustratively, NAH was dissolved in 2 M sodium hydroxide solution to a final concentration of 10 mg/mL and heated at 60° C. for 2 to 24 hours. By changing the heating time, de-N-acetylated heparosan having different de-acetylation degree was prepared.

Next, various lots of N-sulfated heparosan was prepared by N-sulfating this N-de-acetylated heparosan in accordance with the aforementioned method of Leali, D. et al. Illustratively, after neutralizing the liquid in which de-N-acetylation reaction of NAH was completed (contains de-N-acetylated heparosan), sodium carbonate and sulfur trioxide-pyridine complex (PSTC) were added thereto to obtain respective final concentrations of 15 mM and 10 mM and incubated at 40° C. Thereafter, 2.5 mM (final concentration)-corresponding PSTC was added every 1 hour to carry out the reaction for 5 hours. Accordingly, 9 lots of N-sulfated heparosan were obtained. These were used as the substances to be tested.

The monoclonal antibody F58-10E4 (final concentration: 1 µg/mL) and the 9 lots of N-sulfated heparosan (20 µg/well; a value corrected based on the uronic acid content obtained by the carbazole method) were added to the plate to which HSBK was adhered to effect the antigen-antibody reaction under the conditions described in Example 7, and the absorbance was measured by the method described in Example 7. This is a measurement by a so-called inhibition method. When concentration of the N-sulfated heparosan in the antigen-antibody reaction liquid is 0, substantially all of the monoclonal antibody F58-10E4 binds to the adhered HSBK and the detected absorbance becomes high. On the other hand, when excess concentration of N-sulfated heparosan is present in the antigen-antibody reaction liquid, substantially all of the monoclonal antibody F58-10E4 binds to the N-sulfated heparosan in the antigen-antibody reaction liquid (substantially does not bind to the adhered HSBK) and the detected absorbance becomes low.

By regarding the absorbance when concentration of the N-sulfated heparosan in the antigen-antibody reaction liquid is 0 as "inhibition rate 0%", and the absorbance when excess concentration of N-sulfated heparosan is present in the antigen-antibody reaction liquid as "inhibition rate 100%", the inhibition ratio was calculated on the 9 lots of N-sulfated heparosan. The results are shown in Table 1. In this connection, results of the case of the use of HSBK instead of the N-sulfated heparosan are also shown therein.

In this connection, the "Mw" and "Mn" in Table 1 are values calculated by the method described in Example 1(1). Additionally, the mass ratio (%) of the "deNAc-0S" (an NAH-constituting disaccharide unit (GlcA-GlcN) wherein the N-position is de-sulfated and which does not keep sulfate group), "0S" (an NAH-constituting disaccharide unit (GlcA-GlcN) which does not keep sulfate group) and "NS" (an NAH-constituting disaccharide unit (GlcA-GlcN) wherein the N-position is sulfated) in the N-sulfated heparosan molecule of each lot was obtained by an ion exchange chromatography. Conditions and the like of the ion exchange chromatography are as follows.

50 µl of the solution after the digestion with enzymes degrading sulfated polysaccharide or molecular weight-reduced sulfated polysaccharide (a mixture of heparitinase, heparitinase I and heparitinase II (all mfd. by Seikagaku Corporation)) was analyzed using HPLC (IRIKA, Model 852). The absorbance at 232 nm was measured using a strong anion exchange chromatography column (Dionex Corporation, CarboPac PA-1 column 4.0 mm×250 mm). At a flow rate of 1 ml/min, this was carried out in accordance with the method which uses a lithium chloride-incorporated gradient system (50 mM→2.5 M) (kariya, et al., *Comp. Biochem.*

*Physiol.*, 103 B, 473, (1992)) using tetra- to dodeca-saccharide standards as the basis (Yamada, et al., *J. Biol Chem.*, 270, 8696 8706, (1995)).

In this connection, the N-sulfated heparosan of lot 4 and lot 5 having high ratio of de-acetylated disaccharide (deNAc-0S) was again N-sulfated in accordance with the aforementioned method. Additionally, the N-sulfated heparosan of lots 1, 3 and 4 was again N-sulfated by treating with the NDST enzyme liquid by the following method;

A solution prepared by diluting the NDST enzyme liquid 10 times with a solution containing 50 mM HEPES (pH 7.5), 1% Triton X-100, 1 mM $MnCl_2$, 10 mM $MgCl_2$ and 0.1 mM PAPS is added to the N-sulfated heparosan and incubated at 37° C. for 1 hour.

The inhibition rates of these substances were also calculated in the same manner. The results obtained using those which were again N-sulfated by the NDST enzyme liquid are shown in the "NDST" in Table 1, and the results obtained using those which were again sulfated by the sulfur trioxide-pyridine complex (PSTC) are shown in the "Re-NS" in Table 1, respectively.

TABLE 1

| Lot | GPC-HPLC | | SAX-HPLC (%) | | | Inhibition rate (%) | | |
|---|---|---|---|---|---|---|---|---|
| No. | Mw (kDa) | Mw/Mn | deNAc-OS | OS | NS | No treatment | NDST | Re-NS |
| 1 | 4.5 | 1.57 | 32.6 | 0.0 | 67.4 | 27 | 21 | |
| 2 | 11.2 | 1.61 | 21.2 | 2.3 | 76.5 | 68 | | |
| 3 | 8.5 | 1.51 | 35.5 | 0.9 | 63.6 | 0 | 63 | |
| 4 | 30.5 | 1.30 | 34.9 | 44.9 | 20.1 | 21 | 92 | 99 |
| 5 | 25.2 | 1.42 | 38.7 | 25.2 | 36.2 | 29 | | 98 |
| 6 | 33.0 | 1.28 | 10.4 | 41.7 | 47.9 | 98 | | |
| 7 | 28.1 | 1.38 | 18.5 | 17.8 | 63.7 | 99 | | |
| 8 | 21.9 | 1.48 | 18.1 | 3.0 | 78.9 | 96 | | |
| 9 | 6.6 | 1.62 | 18.9 | 1.7 | 79.4 | 46 | | |
| HSBK | | | | | | 99 | | |

From the results of lots 2, 6, 7, 8 and 9 in Table 1, it was shown that the monoclonal antibody F58-10E4 recognizes an N-sulfated heparosan having a weight average molecular weight of 20 kDa or more and also having 45% or more of the N-sulfate structure (NS) similar to heparan sulfate. Also, the N-sulfated heparosan in which the de-acetylated structure (deNAc-0S) exceeded 30% was not recognized by said antibody even when the NS was present in 60% or more, but its reactivity was improved by its N-sulfation by NDST (the result of lot 3). Additionally, reactivity of the lot 4 in which the deNAc-0S exceeded 30% for said antibody was low, but the reactivity became similar to the heparan sulfate by its N-sulfation by NDST or chemical re-N-sulfation. Based on this, it was shown that those which have a weight average molecular weight of 20 kDa or more and in which the de-acetylated structure exceeded 30% are preferable, and the de-acetylated structure exceeded 35% are more preferable, as the N-acetylated heparosan derivative to be used as the substrate (substance to be adhered) in measuring the ST activity in the present invention.

Example 14

Preparation of the ND Detection Kit of the Present Invention

The ND detection kit of the present invention consisting of the following construction was prepared.
1. One NAH-SS-BSA-adhered plate produced in Example 2
2. One bottle of monoclonal antibody JM403
3. One bottle of HRP-labeled goat anti-mouse immunoglobulin G+M antibody
4. One bottle of TMB solution
5. One bottle of reaction stopping liquid described in Example 5
6. One bottle of enzyme reaction liquid 1 described in Example 5
7. One bottle of washing liquid described in Example 5
8. One set of NDST standard solutions Example 15

Preparation of the ST Detection Kit of the Present Invention

The ST detection kit of the present invention consisting of the following construction was prepared.
1. One NAH-SS-BSA-adhered plate produced in Example 2
2. One bottle of monoclonal antibody F58-10E4
3. One bottle of HRP-labeled goat anti-mouse immunoglobulin U+M antibody
4. One bottle of TMB solution
5. One bottle of reaction stopping liquid described in Example 5
6. One bottle of enzyme reaction liquid 2 described in Example 7
7. One bottle of washing liquid described in Example 5
8. One set of NDST standard solutions Example 16

Preparation of the NDST Detection Kit of the Present Invention

The NDST detection kit of the present invention consisting of the following construction was prepared.
1. One NAH-SS-BSA-adhered plate produced in Example 2
2. One bottle of monoclonal antibody JM403
3. One bottle of monoclonal antibody F58-10E4
4. One bottle of HRP-labeled goat anti-mouse immunoglobulin G+M antibody
5. One bottle of TMB solution
6. One bottle of reaction stopping liquid described in Example 5
7. One bottle of enzyme reaction liquid 1 described in Example 5
8. One bottle of enzyme reaction liquid 2 described in Example 7
9. One bottle of washing liquid described in Example 5
10. One set of NDST standard solutions

Example 17

Preparation of the ND Detection Kit of the Present Invention

The ND detection kit of the present invention was prepared by changing the "NAH-SS-BSA-adhered plate produced in Example 2" in Example 14 to the "plate to which the NAH-biotin produced in Example 9 was adhered via avidin".

Example 18

Preparation of the ST Detection Kit of the Present Invention

The ST detection kit of the present invention was prepared by changing the "NAH-SS-BSA-adhered plate produced in Example 2" in Example 15 to the "plate to which the NAH-biotin produced in Example 9 was adhered via avidin".

Example 19

Preparation of the NDST Detection Kit of the Present Invention

The NDST detection kit of the present invention was prepared by changing the "NAH-SS-BSA-adhered plate produced in Example 2" in Example 16 to the "plate to which the NAH-biotin produced in Example 9 was adhered via avidin".

Test Example 1

Measurement of ND Activity Using Sandwich ELISA (1) Production of Plate for Sandwich ELISA Monoclonal antibody JM403 (Seikagaku Corporation) was diluted with PBS(−) to 20 µg/ml. 50 µl of the solution after this dilution was added to each well of MaxiSorp (registered trademark) 96 well microplate (mfd. by NALGE NUNC) and allowed to stand still at 4° C. for 14 to 18 hours, thereby effecting uniform coating on the surface of the wells.

After washing this plate twice with PBS(−), Immunoassay stabilizer (mfd. by Advanced Biotechnologies) containing 0.05% Proclin (registered trademark) 300 (mfd. by SUPELCO) were respectively added thereto as a blocking and as an antiseptic, and allowed to stand still at room temperature for 2 hours, After the standing, the plate in which the monoclonal antibody JM403 was adhered to its wells was obtained by sufficiently removing the blocking substance and drying it at 37° C. for 2 hours. The plate was stored in a refrigerator by sealing in an aluminum laminate bag together with a desiccant.

(2) Production of Biotin-Labeled JM403

Monoclonal antibody JM403 (Seikagaku Corporation) was dialyzed overnight against 0.1 M carbonate buffer (pH 8.5), recovered and then allowed to undergo the reaction with LC-biotin (mfd. by Pierce) which had been dissolved in 0.1 µM carbonate buffer to a concentration of 1 mg/ml, at a mass ratio of 80:1 (monoclonal antibody JM403: LC-biotin) by stirring at room temperature for 4 hours. The solution after the reaction was dialyzed overnight against PBS(−). The solution after the dialysis was recovered and stored in a refrigerator by adding sodium azide (mfd. by Wako Pure Chemical Industries) thereto to a concentration of 0.05%. Consequently, biotin-labeled monoclonal antibody JM403 (to be referred to as "biotin-labeled JM403" hereinafter) was obtained.

(3) Measurement of ND Activity by Sandwich ELISA

30 µl of a solution of pH 6.5 containing 0.05 M MES, 10 mM $MnCl_2$ and 1% Triton X-100, 20 µl of NDST enzyme stock solution, 10 µl of a solution in which NAH was dissolved to a concentration of 1000, 500, 250, 125 or 62.5 µg/ml and 40 µl of distilled water were added to a test tube and allowed to undergo the enzyme reaction by standing still at 37° C. for 60 minutes. As a blank, 10 µl of distilled water was added instead of the NAH solution and allowed to undergo the reaction in the same manner.

After the reaction, the enzyme reaction was terminated by adding 50 µl of 50 mM Tris solution (pH 9.0) containing 450 mM NaCl (to be referred to as "enzyme reaction stopping liquid" hereinafter).

The aforementioned plate for sandwich ELISA was washed three times with 300 µl of the washing liquid. Thereafter, 100 µl of the enzyme reaction stopping liquid was added to each well and allowed to stand still at 37° C. for 60 minutes to effect formation of an antigen-adhered antibody complex.

After the reaction, the wells were washed three times with the washing liquid, and 100 µl of the solution of the biotin-labeled JM403 which was adjusted to 1 µg/ml with PBS(−) containing 1% BSA and 0.05% polyoxyethylene (20) sorbitan monolaurate (to be referred to as "reaction liquid 2" hereinafter) was added to each well in. Thereafter, the plate was allowed to stand still at 37° C. for 60 minutes to effect formation of a sandwich-shaped antibody-antigen-adhered antibody complex.

After the reaction, the wells were washed three times with the washing liquid, and 100 µl of a solution of HRP-labeled streptoavidin (mfd. by Pierce) diluted 1000 times with the reaction liquid 2 was added to each well. Thereafter, the plate was allowed to stand still at ordinary temperature for 30 minutes to effect formation of a biotin-labeled sandwich-shaped complex-streptoavidin complex.

After the reaction, this plate was washed three times with the washing liquid and 100 µl of a TV solution (mfd. by MOSS) as the substrate of peroxidase was added to each well to undergo the reaction at 37° C. for 15 minutes to effect development of a color. Thereafter, the reaction was terminated by adding 100 µl of 1 M HCl (manufactured by Wako Pure Chemicals) to each well, and then absorbance of the TMB degradation product at a wavelength of 450 nm (control wavelength 630 nm) was measured by a well reader SK 603 (registered trademark; available from Seikagaku Corporation).

The monoclonal antibody JM403 recognizes the GlcN residues of NAH (that is, de-N-acetylated GlcNAc residues). When the ND activity is high, the de-N-acetylated sites of NAH are increased, and since this de-N-acetylated moiety can be detected by sandwiching it with the monoclonal antibody JM403 and the biotin-labeled JM403, the degree of de-N-acetylation (ND activity) can be detected thereby. Accordingly, the reactivity detected by sandwiching it with the monoclonal antibody JM403 and the biotin-labeled JM403 was expressed as the ND activity in this Test Example.

This ND activity was calculated by subtracting the absorbance of blank from the measured absorbance. The results are shown in FIG. 9.

Figure 9:
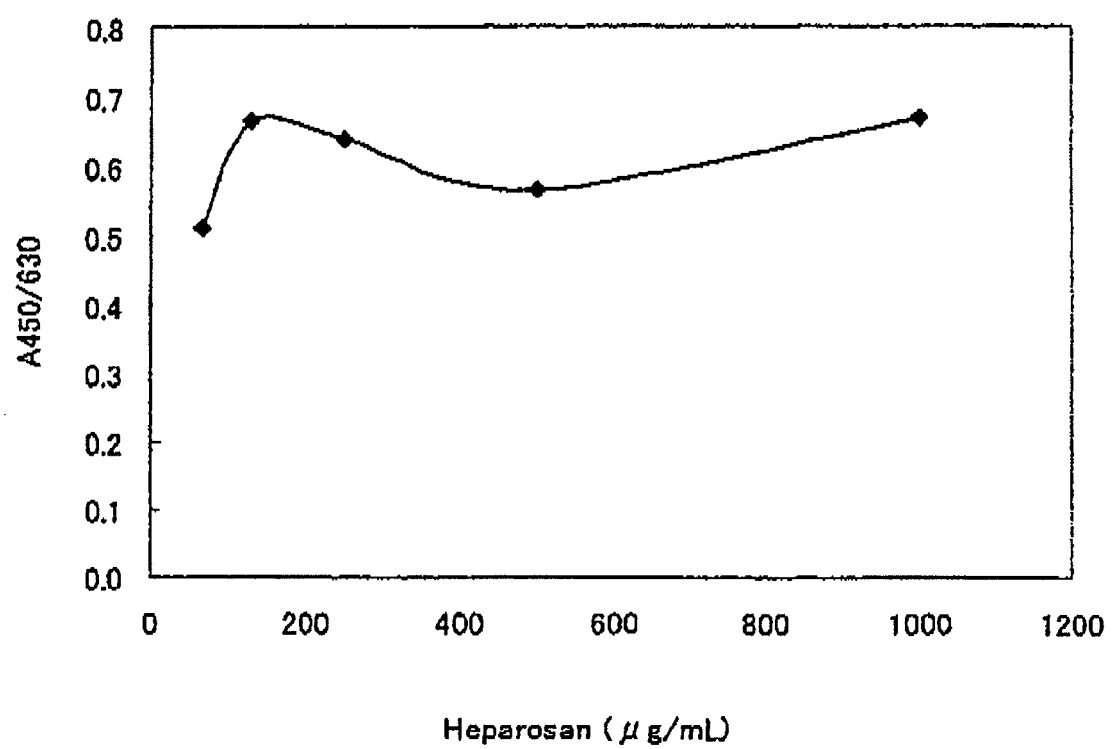
FIG. 9 shows a result of the detection of ND activity using sandwich ELISA.

From FIG. 9, although the ND activity was observed, the activity did not depend on the dose of NAH. Additionally, since its absorbance was low in comparison with the case in which the NAH-SS-BSA-adhered plate or NAH-COOH-BSA-adhered plate was used (approximately from 0.6 to 0.7), it was shown that the detection of ND activity by the sandwich ELISA method shows low sensitivity.

While the present invention has been describe in detail and with reference to specific embodiments thereof, it will be apparent to one skilled in the art that various changes and modifications can be made therein without departing from the spirit and scope of the present invention.

This application is based on a Japanese patent application filed on Jun. 28, 2005 (Japanese Patent Application No. 2005-188973), the entire contents thereof being thereby incorporated by reference. All references cited herein are incorporated as a whole.

Industrial Applicability

The present invention can be applied to the detection of ND activity, ST activity or NDST activity. Also, the present invention can also be applied to the screening of a substance which changes activity of ND, ST or NDST and can also be applied thereby to the screening and the like of new medicinal raw materials and the like. Additionally, the present invention can also be applied to the detection of diseases caused by the abnormal activities of enzymes such as ND ST, detection of risks thereof, understanding of morbid states and the like.

The invention claimed is:

1. A method for detecting N-deacetylase/N-sulfotransferase activity in a sample, which comprises detecting N-deacetylase activity in the sample and also detecting N-sulfotransferase activity in the sample,
wherein the detection of N-deacetylase activity comprises the steps (a) and (b):
step (a): allowing the sample to contact with a solid phase on which a modified polysaccharide has been adhered;
step (b): detecting de-N-acetylation in the modified polysaccharide adhered to the solid phase;
wherein the detecting de-N-acetylation is carried out by allowing a protein that binds to de-N-acetylated glucosamine, but not to N-acetylated glucosamine, to contact with said modified polysaccharide, and determining the binding of said protein that binds to de-N-acetylated glucosamine to said modified polysaccharide;
wherein the detecting N-sulfotransferase activity comprises steps (c) and (d):
step (c): allowing the sample and a sulfate group donor to contact the solid phase on which the modified polysaccharide has been adhered; and
step (d): detecting N-sulfation in the modified polysaccharide adhered to the solid phase;
wherein the detecting of N-sulfation is carried out by allowing a protein that binds to N-sulfated glucosamine, but not to de-N-sulfated glucosamine, to contact with said modified polysaccharide, and determining the binding of said protein that binds to N-sulfated glucosamine to said modified polysaccharide;
wherein the modified polysaccharide comprises a binding substance covalently bound to the non-reducing end or the carboxyl group of N-acetyl heparosan or a derivative thereof, wherein said binding substance interacts directly with said solid phase;
and wherein said binding substance is selected from the group consisting of (a) and (b):
(a) a protein; and
(b) biotin,
and wherein the derivative of N-acetyl heparosan is selected from the group consisting of N-desulfated/N-acetylated heparin and N-desulfated/N-acetylated heparan sulfate.

2. The detection method according to claim 1, wherein said protein that binds to de-N-acetylated glucosamine is an antibody.

3. The detection method according to claim 1, wherein said protein that binds to N-sulfated glucosamine residue is an antibody.

4. The detection method according to claim 3, wherein the antibody is monoclonal antibody F58-10E4 or monoclonal antibody HepSS-1.

5. The detection method according to claim 1, wherein said binding substance is selected from the group consisting of albumin and biotin.

* * * * *